US 11,737,705 B2

United States Patent
Nakashima et al.

(10) Patent No.: US 11,737,705 B2
(45) Date of Patent: Aug. 29, 2023

(54) IMPLANT INSTALLATION STRENGTH EVALUATION METHOD, IMPLANT INSTALLATION STRENGTH EVALUATION DEVICE, AND PROGRAM

(71) Applicants: KEIO UNIVERSITY, Tokyo (JP); NATIONAL INSTITUTES FOR QUANTUM AND RADIOLOGICAL SCIENCE AND TECHNOLOGY, Chiba (JP)

(72) Inventors: Daisuke Nakashima, Tokyo (JP); Takeo Nagura, Tokyo (JP); Masaharu Nishikino, Kyoto (JP); Noboru Hasegawa, Kyoto (JP); Katsuhiro Mikami, Kyoto (JP); Toshiyuki Kitamura, Kyoto (JP); Shuji Kondo, Kyoto (JP); Hajime Okada, Kyoto (JP); Yoshinori Shimada, Osaka (JP)

(73) Assignees: KEIO UNIVERSITY, Tokyo (JP); NATIONAL INSTITUTES FOR QUANTUM AND RADIOLOGICAL SCIENCE AND TECHNOLOGY, Chiba (JP)

( * ) Notice: Subject to any disclaimer, the term of this patent is extended or adjusted under 35 U.S.C. 154(b) by 607 days.

(21) Appl. No.: 16/647,069

(22) PCT Filed: Sep. 13, 2018

(86) PCT No.: PCT/JP2018/033978
§ 371 (c)(1),
(2) Date: Mar. 13, 2020

(87) PCT Pub. No.: WO2019/054442
PCT Pub. Date: Mar. 21, 2019

(65) Prior Publication Data
US 2020/0205730 A1 Jul. 2, 2020

(30) Foreign Application Priority Data

Sep. 14, 2017 (JP) .................................. 2017-177109

(51) Int. Cl.
*A61B 5/00* (2006.01)
*A61C 8/00* (2006.01)
(Continued)

(52) U.S. Cl.
CPC .......... *A61B 5/4851* (2013.01); *A61B 5/0051* (2013.01); *A61B 5/0088* (2013.01);
(Continued)

(58) Field of Classification Search
CPC ........................... A61B 5/4851; A61B 5/0051
See application file for complete search history.

(56) References Cited

U.S. PATENT DOCUMENTS

2002/0143268 A1* 10/2002 Meredith .............. A61B 5/1111
600/552
2002/0177790 A1 11/2002 Meredith et al.
(Continued)

FOREIGN PATENT DOCUMENTS

| CN | 102440759 A | 5/2012 |
| CN | 104254300 A | 12/2014 |

(Continued)

OTHER PUBLICATIONS

May 11, 2021 Extended Search Report issued in European Patent Application No. 18856270.6.
(Continued)

*Primary Examiner* — Andrew Yang
(74) *Attorney, Agent, or Firm* — Oliff PLC

(57) ABSTRACT

An implant installation strength evaluation method includes a step of vibrating an implant, a step of measuring time series data of the number of vibrations and vibration
(Continued)

strengths of the implant vibrated in the vibrating step, and a step of deriving information indicating an index of an installation strength of the implant based on the time series data of the number of vibrations and vibration strengths of the implant.

17 Claims, 14 Drawing Sheets

(51) Int. Cl.
*A61F 2/46* (2006.01)
*G01N 3/06* (2006.01)

(52) U.S. Cl.
CPC ............ *A61C 8/009* (2013.01); *A61F 2/4657* (2013.01); *G01N 3/068* (2013.01); *A61B 2562/0219* (2013.01); *A61F 2002/4666* (2013.01)

(56) References Cited

U.S. PATENT DOCUMENTS

| | | | | |
|---|---|---|---|---|
| 2009/0264754 | A1* | 10/2009 | Dahl | A61B 8/0875 600/438 |
| 2016/0081764 | A1* | 3/2016 | Yasushi | A61C 17/20 433/119 |

FOREIGN PATENT DOCUMENTS

| | | |
|---|---|---|
| CN | 104887235 A | 9/2015 |
| CN | 106037662 A | 10/2016 |
| JP | H02-246923 A | 10/1990 |
| JP | H07-190745 A | 7/1995 |
| JP | 2006-527627 A | 12/2006 |
| JP | 2009-156700 A | 7/2009 |
| JP | 2009-536319 A | 10/2009 |
| JP | 2013-072688 A | 4/2013 |
| JP | 2014-135974 A | 7/2014 |
| JP | 2017-144061 A | 8/2017 |
| WO | 2004/110272 A1 | 12/2004 |
| WO | 2015/059956 A1 | 4/2015 |

OTHER PUBLICATIONS

Dec. 18, 2018 International Search Report issued in International Patent Application No. PCT/JP2018/033978.
Mar. 19, 2021 Office Action issued in Chinese Patent Application No. 201880059323.4.
Jan. 4, 2023 Office Action issued in Japanese Patent Application No. 2019-542284.

* cited by examiner

| PEAK FREQUENCY | EMBEDDING TORQUE |
|---|---|
| a1 | b1 |
| a2 | b2 |
| a3 | b3 |
| ... | ... |

| PEAK FREQUENCY | PULLING FORCE |
|---|---|
| a1 | c1 |
| a2 | c2 |
| a3 | c3 |
| ... | ... |

IMPLANT INSTALLATION STRENGTH EVALUATION METHOD, IMPLANT INSTALLATION STRENGTH EVALUATION DEVICE, AND PROGRAM

TECHNICAL FIELD

Embodiments of the present invention relate to an implant installation strength evaluation method, an implant installation strength evaluation device, and a program.

Priority is claimed on Japanese Patent Application No. 2017-177109, filed Sep. 14, 2017, the content of which is incorporated herein by reference.

BACKGROUND ART

In an implant treatment operation in which an implant such as an artificial joint is installed in a human bone, an installation strength of the implant is judged by an operating surgeon's knowledge and experience in most cases. Insufficiency of the installation strength of an implant may result in looseness or separation of the implant in the future.

The installation strength of the implant is often evaluated in a non-clinical manner by a destructive test using an embedding torque or an evulsion force in a research stage.

On the other hand, regarding an evaluation technology that is adaptable during a dental implant treatment operation, a technology of measuring a resonance frequency using magnetism is known (for example, refer to Patent Literature 1).

In addition, image diagnosis, such as taking an X-ray, is used in parallel therewith during and after an implant operation. Image diagnosis is mainly used for checking an implant installation position. A technology, in which image diagnosis and a computer analysis technology are combined, of evaluating a fixing strength of an implant is known (for example, refer to Patent Literature 2).

CITATION LIST

Patent Literature

Patent Literature 1

Published Japanese Translation No. 2006-527627 of the PCT International Publication Patent Literature 2

Japanese Unexamined Patent Application, First Publication No. 2014-135974

SUMMARY OF INVENTION

Technical Problem

Magnetic resonance frequency analysis using a magnet is a technique that is adaptable to the field of dentistry targeting the inside of an oral cavity in which a magnet can be easily attached to and detached from an implant. For this reason, it is difficult to adapt magnetic resonance frequency analysis using a magnet to the field of orthopedics requiring a surgical operation deep inside a body.

The present invention has been made in order to solve the foregoing problem, and an object thereof is to provide an implant installation strength evaluation method, an implant installation strength evaluation device, and a program in which the installation strength of an implant can be evaluated.

Solution to Problem (1) According to an aspect of the present invention, there is provided an implant installation strength evaluation method including a step of vibrating an implant, a step of measuring time series data of the number of vibrations and vibration strengths of the implant vibrated in the vibrating step, and a step of deriving information indicating an index of an installation strength of the implant based on the time series data of the number of vibrations and the vibration strengths of the implant.

(2) According to the aspect of the present invention, the implant installation strength evaluation method according to (1) described above further includes a step of acquiring an evaluation result of the installation strength of the implant based on the information indicating the index of the installation strength.

(3) According to the aspect of the present invention, in the implant installation strength evaluation method according to (1) or (2) described above, in the deriving step, a relationship between a frequency, the number of vibrations, and a vibration strength is obtained based on the time series data of the number of vibrations and the vibration strengths of the implant; a frequency corresponding to a predetermined number of vibrations and a predetermined vibration strength is obtained from the obtained relationship between a frequency, the number of vibrations, and a vibration strength; and the information indicating the index of the installation strength of the implant associated with the obtained frequency is obtained from association between the frequency and the information indicating the index of the installation strength of the implant.

(4) According to the aspect of the present invention, in the implant installation strength evaluation method according to any one of (1) to (3) described above, at least one of the steps is controlled and executed by a computer.

(5) According to the aspect of the present invention, in the implant installation strength evaluation method according to (3) or (4) described above, the information indicating the index of the installation strength of the implant is an embedding torque indicating a resistance generated in a bone when the implant is embedded in the bone.

(6) According to the aspect of the present invention, in the implant installation strength evaluation method according to (3) or (4) described above, the information indicating the index of the installation strength of the implant is a pulling force that is a force acting when an artificial joint cup is detached from a bone in a case in which an installation rod is attached to the artificial joint cup attached to the bone and the installation rod is pulled.

(7) According to the aspect of the present invention, in the implant installation strength evaluation method according to any one of (1) to (6) described above, in the vibrating step, the implant is vibrated when the implant is irradiated with a laser beam.

(8) According to the aspect of the present invention, in the implant installation strength evaluation method according to any one of (1) to (6) described above, in the vibrating step, the implant is vibrated by applying a water stream to the implant.

(9) According to the aspect of the present invention, in the implant installation strength evaluation method according to any one of (1) to (6) described above, in the vibrating step, the implant is vibrated by applying a force to the implant.

(10) According to the aspect of the present invention, in the implant installation strength evaluation method according to any one of (1) to (6) described above, in the measuring step, the time series data of the number of vibrations and vibration strengths of the implant vibrated in the vibrating step is measured using an acceleration sensor.

(11) According to the aspect of the present invention, in the implant installation strength evaluation method according to any one of (1) to (6) described above, in the measuring step, the time series data of the number of vibrations and vibration strengths of the implant vibrated in the vibrating step is measured based on a generated sound.

(12) According to the aspect of the present invention, in the implant installation strength evaluation method according to any one of (1) to (6) described above, in the vibrating step, the implant is vibrated when the implant is irradiated with a first laser beam. In the measuring step, the implant is irradiated with a second laser beam, and the time series data of the number of vibrations and strengths of the implant is measured based on the second laser beam reflected by the implant.

(13) According to the aspect of the present invention, in the implant installation strength evaluation method according to any one of (1) to (6) described above, in the vibrating step, the implant is vibrated by applying a water stream to the implant. In the measuring step, the time series data of the number of vibrations and strengths of the implant is measured by applying a water stream to the implant based on a generated sound.

(14) According to the aspect of the present invention, there is provided the implant installation strength evaluation method according to any one of (1) to (6) described above including a step of vibrating an implant, a step of measuring time series data of the number of vibrations and vibration strengths of the implant vibrated in the vibrating step, and a step of deriving information indicating an index of an installation strength of the implant based on the time series data of the number of vibrations and vibration strengths of the implant. Both or any one of the vibrating step and the measuring step is executed by an implant installation strength evaluation device and is executed in a non-contact manner utilizing a laser beam.

(15) According to another aspect of the present invention, there is provided an implant installation strength evaluation device acquiring data using the implant installation strength evaluation method according to any one of (1) to (14) described above. The implant installation strength evaluation device includes a vibration induction unit that vibrates an implant, a measurement unit that measures time series data of the number of vibrations and vibration strengths of the implant vibrated by the vibration induction unit, and a deriving unit that derives information indicating an index of an installation strength of the implant based on the time series data of the number of vibrations and the vibration strengths of the implant measured by the measurement unit.

(16) According to another aspect of the present invention, there is provided an implant installation strength evaluation device acquiring data using the implant installation strength evaluation method according to any one of claims 1 to 12, and 14. The implant installation strength evaluation device includes a vibration induction unit that vibrates an implant, a measurement unit that measures time series data of the number of vibrations and vibration strengths of the implant vibrated by the vibration induction unit, and a deriving unit that derives information indicating an index of an installation strength of the implant based on the time series data of the number of vibrations and the vibration strengths of the implant measured by the measurement unit. Both or any one of the vibration induction unit and the measurement unit performs an action in a non-contact manner utilizing a laser beam.

(17) According to another aspect of the present invention, there is provided a program for acquiring data using the implant installation strength evaluation method according to any one of (1) to (12) and (14) described above by causing a computer to execute a step of vibrating an implant, a step of measuring time series data of the number of vibrations and vibration strengths of the implant vibrated in the vibrating step, and a step of deriving information indicating an index of an installation strength of the implant based on the time series data of the number of vibrations and the vibration strengths of the implant. Both or any one of the vibrating step and the measuring step is executed in a non-contact manner utilizing a laser beam.

ADVANTAGEOUS EFFECTS OF INVENTION

According to embodiments of the present invention, it is possible to provide the implant installation strength evaluation method, the implant installation strength evaluation device, and the program in which the installation strength of an implant can be evaluated.

DESCRIPTION OF EMBODIMENTS

Next, an implant installation strength evaluation method, an implant installation strength evaluation device, and a program of the present embodiment will be described with reference to the drawings. The embodiments described below are merely examples, and embodiments in which the present invention is applied are not limited to the following embodiments.

In all the drawings for describing the embodiments, the same reference signs are applied to parts having the same function, and duplicate description will be omitted.

In addition, the expression "based on XX" used in this application denotes "based on at least XX" and also includes a case based on another element in addition to XX. In addition, "based on XX" is not limited to a case in which XX is used directly and also includes a case based on a state in which XX is subjected to computation or processing. The term "XX" is an arbitrary element (for example, arbitrary information).

In addition, the term "an implant" used in this application indicates a member that is used by being fixed to hard tissue such as a bone and is not limited by the shape and the material thereof. For example, "an implant" includes an implant having a shape such as a bolt shape, a plate shape, a cup shape, or a spherical shape, and materials known in the related art, such as titanium, stainless steel, and ceramics, can be selected suitably.

For example, a pulse laser can be applied as an implant installation strength evaluation system of the embodiments. A laser medium used in the pulse laser is not particularly limited, and a solid laser medium, a liquid laser medium, a gas laser medium or the like known in the related art may be employed suitably. In addition, in the implant installation strength evaluation system of the embodiments, for example, a solid laser medium (Nd:YAG), a gas laser medium (carbonic acid gas), or a liquid laser medium (dye laser) can be employed, and a Nd:YAG laser, a carbonic acid gas laser, a dye laser, or the like can be applied as a laser.

First Embodiment (Implant Installation Strength Evaluation System)

Figure 1:
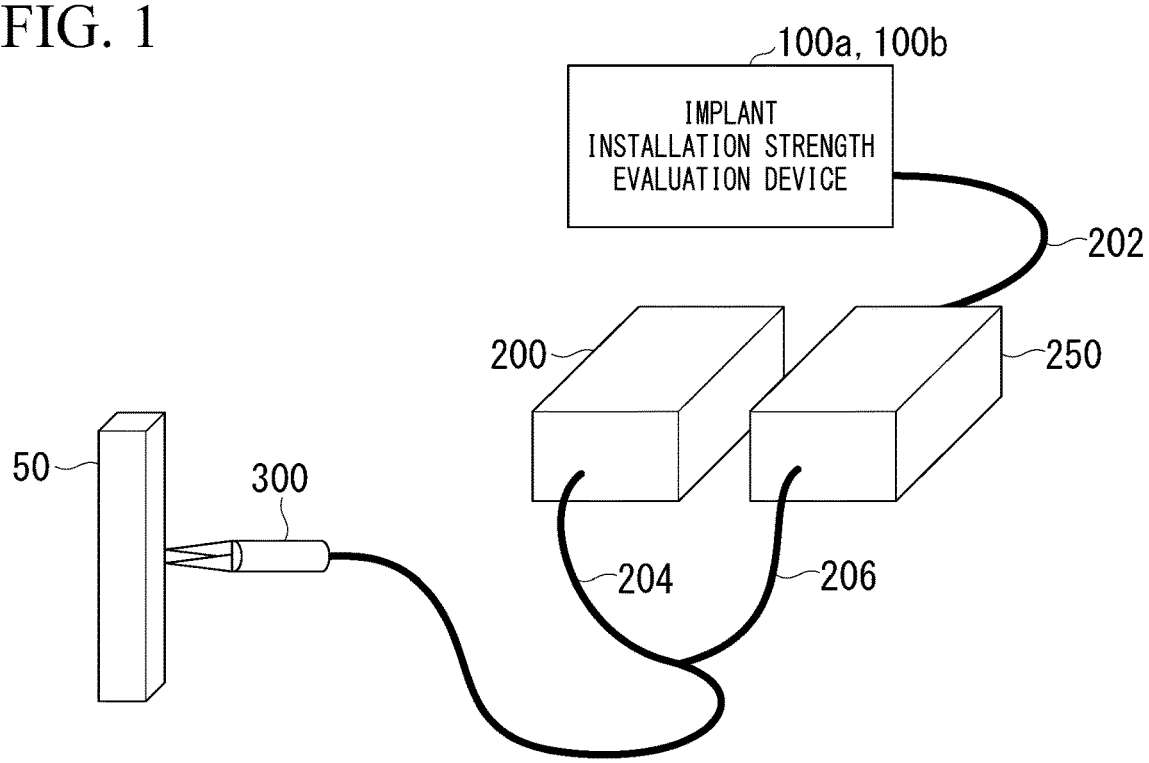
FIG. 1 is a view illustrating an example of an implant installation strength evaluation system of a first embodiment.

FIG. 1 is a view illustrating an example of an implant installation strength evaluation system of a first embodiment. The implant installation strength evaluation system vibrates an evaluation target 50 such as an implant by irradiating it with a laser beam. In the first embodiment, an artificial bone is postulated as an example of the evaluation target 50.

The implant installation strength evaluation system acquires time series data of the number of vibrations and vibration strengths with respect to each vibration frequency of the vibrated evaluation target 50 and derives a frequency spectrum of the number of vibrations and a vibration strength based on the time series data of the number of vibrations and vibration strengths with respect to each of the acquired vibration frequencies. The implant installation strength evaluation system acquires information indicating an index of an installation strength of the evaluation target 50 by analyzing the derived frequency spectrum.

In the first embodiment, description will be continued regarding a case in which an embedding torque is applied as an example of the information indicating the index of the installation strength of the evaluation target 50. The implant installation strength evaluation system acquires an evaluation result indicating whether or not the installation strength of the evaluation target 50 is appropriate based on the acquired embedding torque of the evaluation target 50.

The implant installation strength evaluation system includes an implant installation strength evaluation device 100a, a first laser system 200, a second laser system 250, and an irradiation head 300. The implant installation strength evaluation device 100a and the second laser system 250 are connected to each other through a cable 202. The first laser system 200 and the irradiation head 300 are connected to each other through an optical fiber 204. The second laser system 250 and the irradiation head 300 are connected to each other through an optical fiber 206.

The first laser system 200 generates a laser beam A for inducing vibration in the evaluation target 50 and outputs the generated laser beam A to the optical fiber 204. Specifically, an example of the first laser system 200 is a Nd:YAG laser. Irradiation energy of the laser beam A generated by the first laser system 200 may be set suitably within a range of 1 mJ to 50 mJ, for example. Typically, it may be within a range of 10 mJ to 30 mJ.

The irradiation head 300 irradiates the evaluation target 50 with the laser beam A output by the first laser system 200. Accordingly, the evaluation target 50 vibrates. In addition, in a state in which the evaluation target 50 vibrates, the irradiation head 300 irradiates the evaluation target 50 with a laser beam B1 output by the second laser system 250. The evaluation target 50 reflects the irradiation laser beam B1 from the irradiation head 300. Then, a reflected laser beam B2 is transmitted through the optical fiber 206 from the irradiation head 300 and is output to the second laser system 250.

The second laser system 250 detects vibration generated in the evaluation target 50. The second laser system 250 generates the laser beam B1 for detecting vibration induced in the evaluation target 50 and outputs the generated laser beam B1 to the optical fiber 206. The second laser system 250 acquires the laser beam B2 reflected by the evaluation target 50 from the optical fiber 206 and converts the acquired laser beam B2 into the number of vibrations and a vibration strength. The second laser system 250 outputs the information indicating the number of vibrations and a vibration strength obtained by converting the laser beam B2 to the implant installation strength evaluation device 100a. Specifically, an example of the second laser system 250 is a laser Doppler vibrometer.

The implant installation strength evaluation device 100a acquires the information indicating the number of vibrations and a vibration strength output by the second laser system 250. The implant installation strength evaluation device 100a acquires a frequency spectrum by performing Fourier conversion of the time series data of the number of vibrations and vibration strengths based on the acquired information indicating the number of vibrations and a vibration strength. The implant installation strength evaluation device 100a acquires a frequency (which will hereinafter be referred to as "a peak frequency") at which the number of vibrations and the vibration strength peak from the acquired frequency spectrum. The implant installation strength evaluation device 100a acquires an embedding torque based on the acquired peak frequency.

Here, an embedding torque indicates a resistance generated in a bone when an implant is embedded in the bone. There is concern that if the embedding torque is excessively low, fixing in an initial stage may become weak, and if the embedding torque is excessively high, avascular bone necrosis may be caused around an implant. Therefore, it is possible to evaluate whether or not the installation strength of an implant is appropriate by monitoring the embedding torque.

(Evaluation Target)

An example of the evaluation target 50 will be described.

Figure 2:
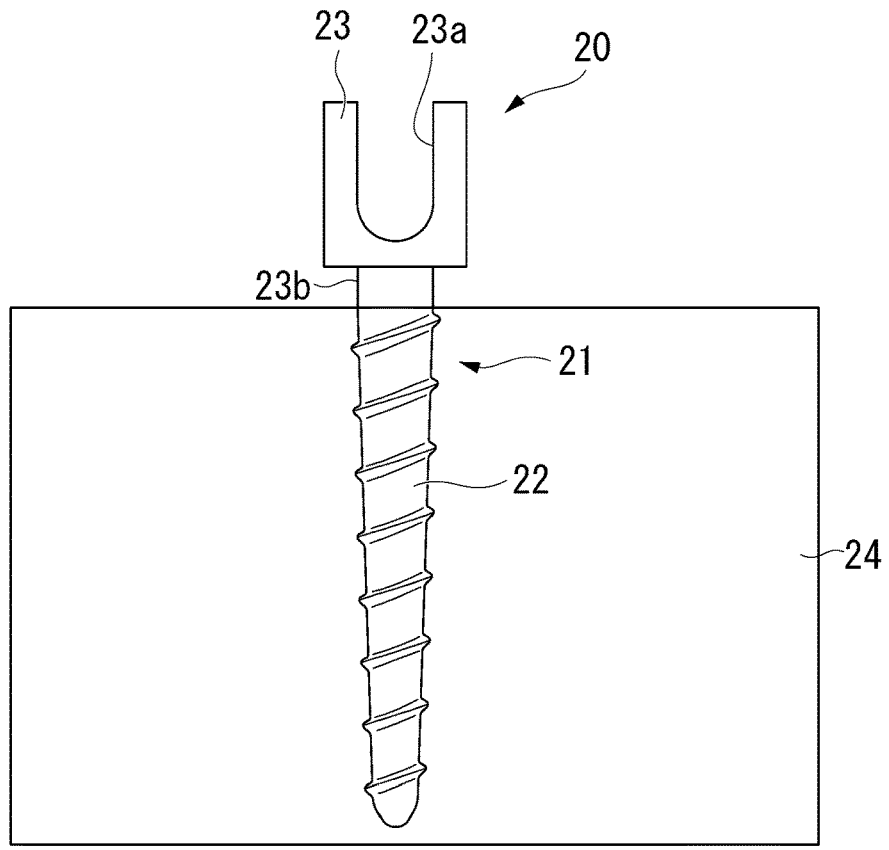
FIG. 2 is a view illustrating an example of an evaluation target of the first embodiment.

FIG. 2 is a view illustrating an example of an evaluation target of the first embodiment. Here, an implant 20 for orthopedics is illustrated as an example of the evaluation target 50. The implant 20 is formed of an implant material and includes a main body 21 used as the evaluation target 50.

The main body 21 has an external shape similar to those of general main bodies and includes a threaded portion 22 which is embedded into a bone 24 (embedding target), and a head portion 23 which is connected to the threaded portion 22. A horizontal hole 23a, through which a spinal fixing rod is inserted, is formed in the head portion 23.

When the evaluation method described above is executed using the implant 20, an embedding hole, in which a thread groove is formed by tapping, serves as a measurement hole, and the implant 20 is temporarily installed in this embedding hole. Temporary installation may be performed by embedding the threaded portion 22 to a postulated embedding depth, or embedding may be performed to a depth at a position shallower than the postulated embedding depth.

A root 23b or the head portion 23 of the implant 20 is irradiated with the laser beam A generated by the first laser system 200 from the irradiation head 300. Moreover, the root 23b or the head portion 23 of the implant 20 is irradiated with the laser beam B1 generated by the second laser system 250 from the irradiation head 300.

Although the constitution is not particularly limited, a case in which the root 23b of the implant B1 is irradiated with the laser beam A and the laser beam B1 will be described herein as an example. An area in the implant 20 to be irradiated with the laser beam A (for example, the area of the root 23b) and an area in the implant 20 to be irradiated with the laser beam B1 (for example, the area of the root 23b) may coincide or may not coincide with each other.

(Implant Installation Strength Evaluation Device)

Figures 3, 4:
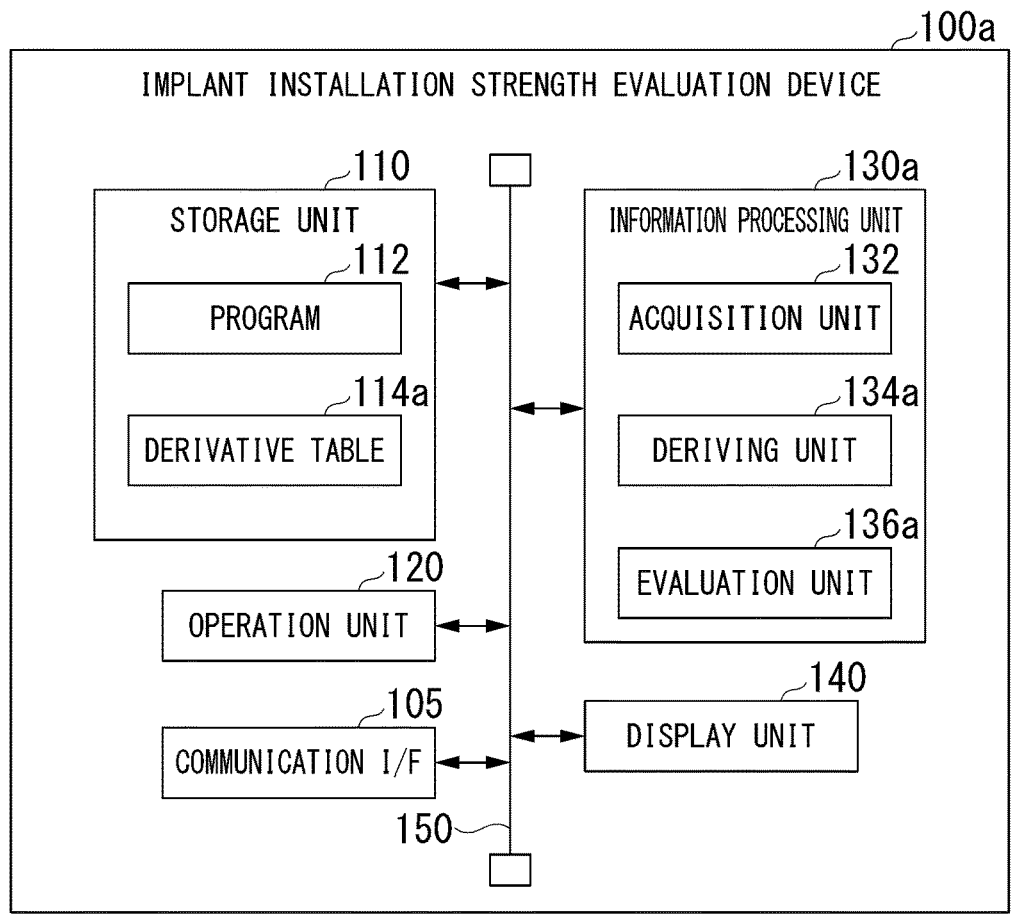
FIG. 3 is a block diagram illustrating an example of an implant installation strength evaluation device of the first embodiment.
FIG. 4 is a view illustrating an example of a derivative table.

FIG. 3 is a block diagram illustrating an example of an implant installation strength evaluation device of the first embodiment.

The implant installation strength evaluation device 100a includes a communication I/F 105, a storage unit 110, an operation unit 120, an information processing unit 130a, a display unit 140, and a bus line 150 for an address bus, a data bus, and the like for electrically connecting each of the constituent elements as illustrated in FIG. 3.

The communication I/F 105 is an I/F between the implant installation strength evaluation device 100a and the second laser system 250. The information indicating the number of vibrations and a vibration strength output by the second laser system 250 is input to the communication I/F 105. The communication I/F 105 acquires the information indicating the number of vibrations and a vibration strength and outputs the acquired information indicating the number of vibrations and a vibration strength to the information processing unit 130a.

For example, the storage unit 110 is realized by a random access memory (RAM), a read only memory (ROM), a hard disk drive (HDD), a flash memory, a hybrid storage device in which a plurality of elements of these are combined, or the like. The storage unit 110 stores a program 112 executed by the information processing unit 130a, and a derivative table 114a.

(Derivative Table)

FIG. 4 is a view illustrating an example of a derivative table. The derivative table 114a is a table in which peak frequencies and embedding torques are associated with each other. The peak frequency is a peak frequency acquired from the frequency spectrum of the number of vibrations and a vibration strength of the evaluation target 50 when the evaluation target 50 is vibrated by the laser beam A. The embedding torque is an embedding torque which is associated with the peak frequency of the vibrated evaluation target 50. Association between a peak frequency and an embedding torque of the evaluation target 50 will be described below. In the example illustrated in FIG. 4, a peak frequency "a1" and an embedding torque "b1" are stored in association with each other.

Returning to FIG. 3, description will be continued. For example, the operation unit 120 is constituted of a touch panel or the like. The operation unit 120 detects a touch operation with respect to a screen displayed by the display unit 140 and outputs a detection result of a touch operation to the information processing unit 130a. A touch operation includes an operation of starting evaluation of an implant, and the like. When an operation of starting evaluation of an implant is detected, the operation unit 120 outputs information indicating starting of evaluation of an implant to the information processing unit 130a.

For example, the entirety or a part of the information processing unit 130a is a functional unit (which will hereinafter be referred to as a software functional unit) realized by a processor such as a central processing unit (CPU) executing the program 112 stored in the storage unit 110. The entirety or a part of the information processing unit 130a may be realized by hardware such as a large scale integration (LSI), an application specific integrated circuit (ASIC), or a field-programmable gate array (FPGA) or may be realized by a combination of a software functional unit and hardware.

For example, the information processing unit 130a includes an acquisition unit 132, a deriving unit 134a, and an evaluation unit 136a.

The acquisition unit 132 acquires the information indicating starting of evaluation of an implant output by the operation unit 120. The acquisition unit 132 acquires the information indicating the number of vibrations and a vibration strength of the evaluation target 50 output by the communication I/F 105. The acquisition unit 132 outputs the acquired information indicating the number of vibrations and a vibration strength of the evaluation target 50 to the deriving unit 134a.

The deriving unit 134a derives a frequency spectrum of a vibration strength with respect to each of the vibration frequencies of the evaluation target 50 based on the information indicating the number of vibrations and a vibration strength of the evaluation target 50 output by the acquisition unit 132. The deriving unit 134a acquires a peak frequency at which the vibration strength peaks in the derived frequency spectrum. Specifically, the deriving unit 134a acquires a peak frequency at which the vibration strength peaks within a range of 2 kHz to 10 kHz. Alternatively, when x indicates the frequency, the deriving unit 134a has a function f(x) expressing the frequency spectrum. The deriving unit 134a designates a frequency range of x=1 kHz to 20 kHz and more preferably designates a frequency range of x=2 kHz to 10 kHz because the component of a high-frequency vibration strength is invariable.

The deriving unit 134a obtains x satisfying $df(x)/dx=0$ in which the function f(x) is differentiated by x and $d^2f(x)/dx^2<0$ in which the function f(x) is differentiated twice by x. The deriving unit 134a has f(n) (n=0, 1, 2, and so on) in order from x having a smaller value. The deriving unit 134a acquires the smallest f(n) satisfying $f(n)>\max f(x) \times C$ (max f(x) indicates the largest value of f(x), and C indicates an arbitrary constant for determining a threshold).

The deriving unit 134a acquires the embedding torque associated with the acquired peak frequency from association between peak frequencies and embedding torques included in the derivative table 114a stored in the storage unit 110. The deriving unit 134a outputs information indicating the acquired embedding torque to the evaluation unit 136a.

The evaluation unit 136a acquires the information indicating the embedding torque which is output by the deriving unit 134a. The evaluation unit 136a determines whether or not the acquired embedding torque is within a range set in advance. When the acquired embedding torque is included within the range set in advance, the evaluation unit 136a acquires an evaluation result in which the embedding torque is appropriate. When the acquired embedding torque is not included within the range set in advance, the evaluation unit 136a acquires an evaluation result in which the embedding torque is inappropriate. The evaluation unit 136a outputs the evaluation result of the embedding torque to the display unit 140.

The display unit 140 acquires the evaluation result of the embedding torque which is output by the evaluation unit 136a. The display unit 140 displays the acquired evaluation result of the embedding torque.

(Operation of Implant Installation Strength Evaluation Device)

Figure 5:
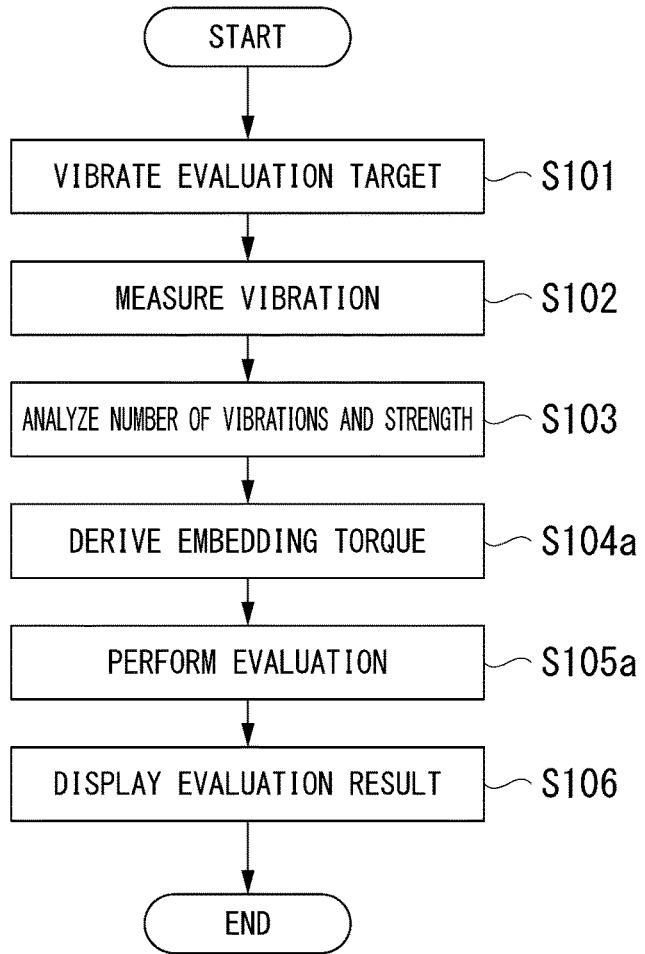
FIG. 5 is a view illustrating an example of operation of the implant installation strength evaluation device of the first embodiment.

FIG. 5 is a view illustrating an example of operation of the implant installation strength evaluation device of the first embodiment.

(Step S101)

The first laser system 200 vibrates the evaluation target 50. Specifically, the first laser system 200 generates the laser beam A and outputs the generated laser beam A to the optical fiber 204. A user fixes the irradiation head 300 such that the evaluation target 50 is irradiated with the irradiation laser beam A from the irradiation head 300. The irradiation head 300 irradiates the evaluation target 50 with the laser beam A output by the first laser system 200. Accordingly, vibration is induced by the laser beam A, and the evaluation target 50 vibrates.

(Step S102)

The second laser system 250 measures vibration generated in the evaluation target 50. Specifically, the second laser system 250 generates the laser beam B1 for detecting vibration induced in the evaluation target 50 and outputs the generated laser beam B1 to the optical fiber 206. A user fixes the irradiation head 300 such that the evaluation target 50 is irradiated with the irradiation laser beam B from the irradiation head 300.

The irradiation head 300 irradiates the evaluation target 50 with the laser beam B1 output by the second laser system 250. The second laser system 250 acquires the laser beam B2, which is the reflected laser beam B1 from the evaluation target 50, from the optical fiber 206 and acquires the number of vibrations and a vibration strength based on the acquired laser beam B2. The second laser system 250 outputs the information indicating the number of vibrations and a vibration strength to the implant installation strength evaluation device 100a.

(Step S103)

The acquisition unit 132 of the implant installation strength evaluation device 100a acquires the information indicating the number of vibrations and a vibration strength output by the second laser system 250. The acquisition unit 132 outputs the acquired information indicating the number of vibrations and a vibration strength to the deriving unit 134a.

The deriving unit 134a obtains the frequency spectrum of the number of vibrations and a vibration strength based on the information indicating the number of vibrations and a vibration strength output by the acquisition unit 132. The deriving unit 134a acquires a peak frequency, at which the vibration strength peaks, from the frequency spectrum.

(Step S104a)

The deriving unit 134a of the implant installation strength evaluation device 100a acquires the embedding torque associated with the acquired peak frequency from association between peak frequencies and embedding torques included in the derivative table 114a stored in the storage unit 110. The deriving unit 134a outputs the information indicating the acquired embedding torque to the evaluation unit 136a.

(Step S105a)

The evaluation unit 136a of the implant installation strength evaluation device 100a acquires the information indicating the embedding torque which is output by the deriving unit 134a. When the embedding torque is included within the range set in advance, the evaluation unit 136a acquires a determination result in which the embedding torque is appropriate based on the information indicating the acquired embedding torque. In this case, the installation strength of the evaluation target 50 is evaluated as being appropriate. When the acquired embedding torque is not included within the range set in advance, the evaluation unit 136a acquires a determination result in which the embedding torque is inappropriate. In this case, the installation strength of the evaluation target 50 is evaluated as being inappropriate. The evaluation unit 136a outputs the evaluation result of the installation strength of the evaluation target 50 to the display unit 140.

(Step S106)

The display unit 140 of the implant installation strength evaluation device 100a acquires the evaluation result of the installation strength of the evaluation target 50 output by the evaluation unit 136a. The display unit 140 displays the acquired evaluation result of the installation strength of the evaluation target 50.

According to operation of the implant installation strength evaluation device illustrated in FIG. 5, the implant installation strength evaluation device 100a acquires a peak frequency from the frequency spectrum of the number of vibrations and a vibration strength of the vibrated evaluation target 50. The implant installation strength evaluation device 100a acquires the embedding torque associated with the acquired peak frequency from association between peak frequencies and embedding torques. The implant installation strength evaluation device 100a acquires an evaluation result indicating whether or not the installation strength of the evaluation target 50 is appropriate from the acquired embedding torque.

(Example of Derived Association Between Peak Frequencies and Embedding Torques)

Here, an example of derived association between peak frequencies and embedding torques will be described.

Figure 6:
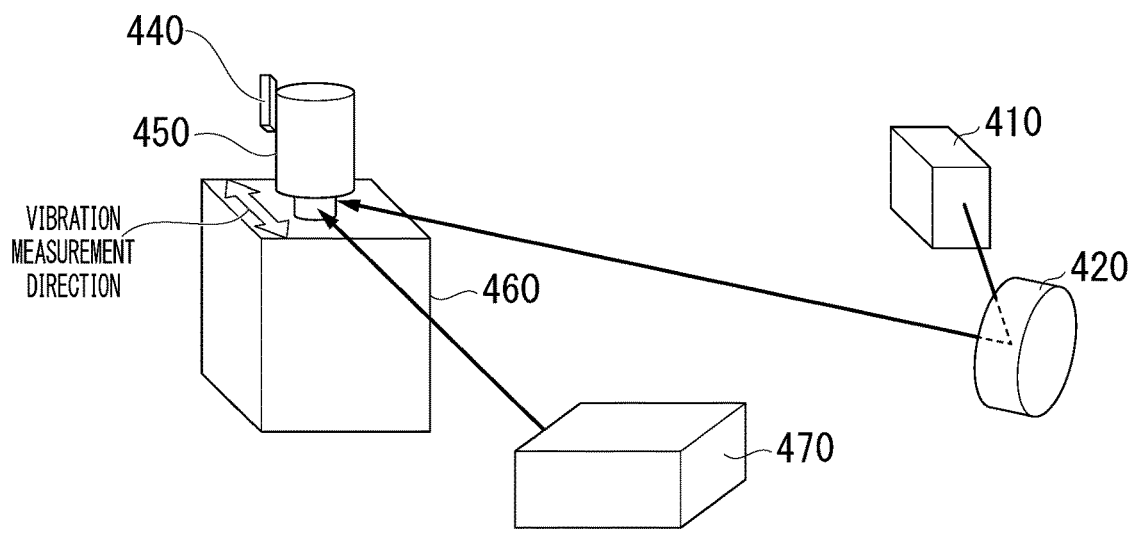
FIG. 6 is a view illustrating a vibration evaluation system in an example (Example 1).

FIG. 6 is a view illustrating a vibration evaluation system in an example (Example 1). The peak frequencies and the embedding torques are associated with each other prior to the processing of the implant installation strength evaluation device 100a evaluating whether or not the installation strength of the evaluation target 50 is appropriate. Then, the association between peak frequencies and embedding torques is stored in the derivative table 114a.

In the vibration evaluation system illustrated in FIG. 6, a plurality of implants fixed to artificial bones at different embedding torques are vibrated when each of the implants is irradiated with a laser beam. Then, the vibration evaluation system obtains frequency spectrums of the vibrated implants and acquires peak frequencies from the obtained frequency spectrums. Then, the vibration evaluation system causes the acquired peak frequencies and the embedding torques to be associated with each other.

The vibration evaluation system includes a first laser system 470, a second laser system 410, a first reflector 420, an acceleration sensor 440, an implant 450, and an artificial bone 460.

The implant 450 is embedded in the artificial bone 460.

The first laser system 470 generates a laser beam for inducing vibration in the implant 450 and irradiates a root of the implant 450 with the generated laser beam. The implant 450 vibrates when the root of the implant 450 is irradiated with a laser beam. Specifically, an example of the first laser system 470 is a Nd:YAG laser. Irradiation energy of the laser beam generated by the first laser system 470 may be set suitably within a range of 10 mJ to 30 mJ, for example. Typically, it may be within a range of 15 mJ to 25 mJ. In addition, a repetitive frequency of the laser is within a range of 5 Hz to 15 Hz. The average number of instances of spectra is within a range of 100 times to 150 times.

The second laser system 410 generates a laser beam for detecting vibration induced in the implant 450 and outputs the generated laser beam. The laser beam output by the second laser system 410 is reflected by the first reflector 420, and the root of the implant 450 is irradiated with the laser beam reflected by the first reflector 420. The direction of the first reflector 420 is adjusted such that the root of the implant 450 is irradiated with the laser beam output by the second laser system 410. The distance between the first reflector 420 and the root of the implant is approximately 1 m.

The implant 450 reflects an irradiation laser beam from the second laser system 410. The laser beam reflected by the implant 450 is reflected by the first reflector 420, and the laser beam reflected by the first reflector 420 is input to the second laser system 410. The vibration evaluation system illustrated in FIG. 6 mainly detects vibration in a direction of 90 degrees with respect to a direction in which the implant 450 is embedded in the artificial bone 460. An example of the second laser system 410 is a laser Doppler vibrometer, and an output thereof is within a range of 0.5 mW to 1.5 mW.

The acceleration sensor 440 is attached to a head portion of the implant 450 and detects vibration induced in the implant 450.

Figure 7A:
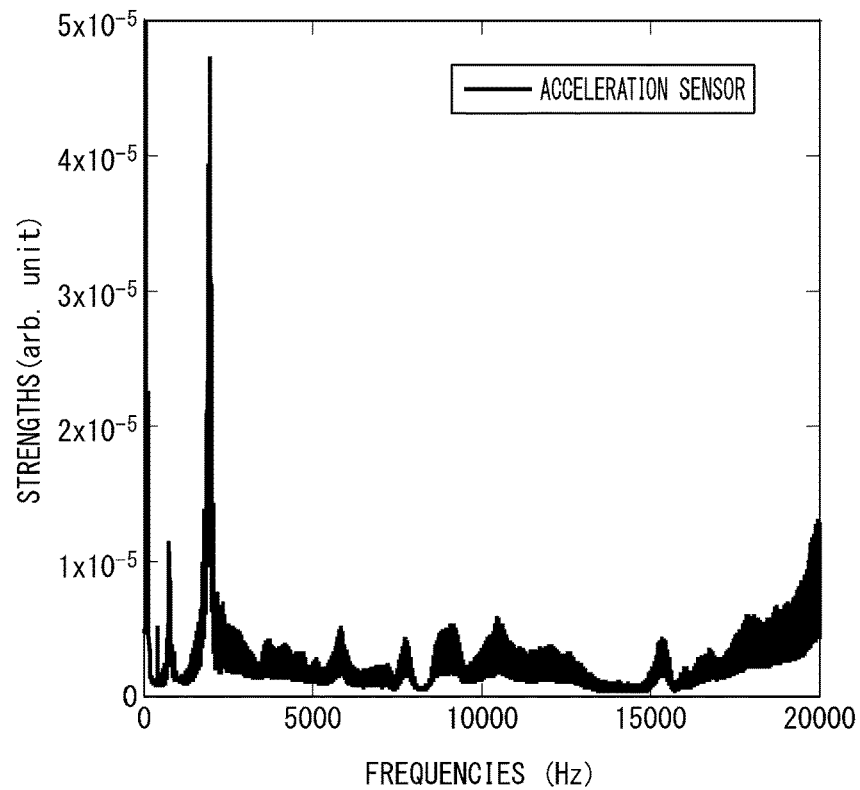
FIG. 7A is a view illustrating a vibration evaluation result in the example (Example 1).
Figure 7B:
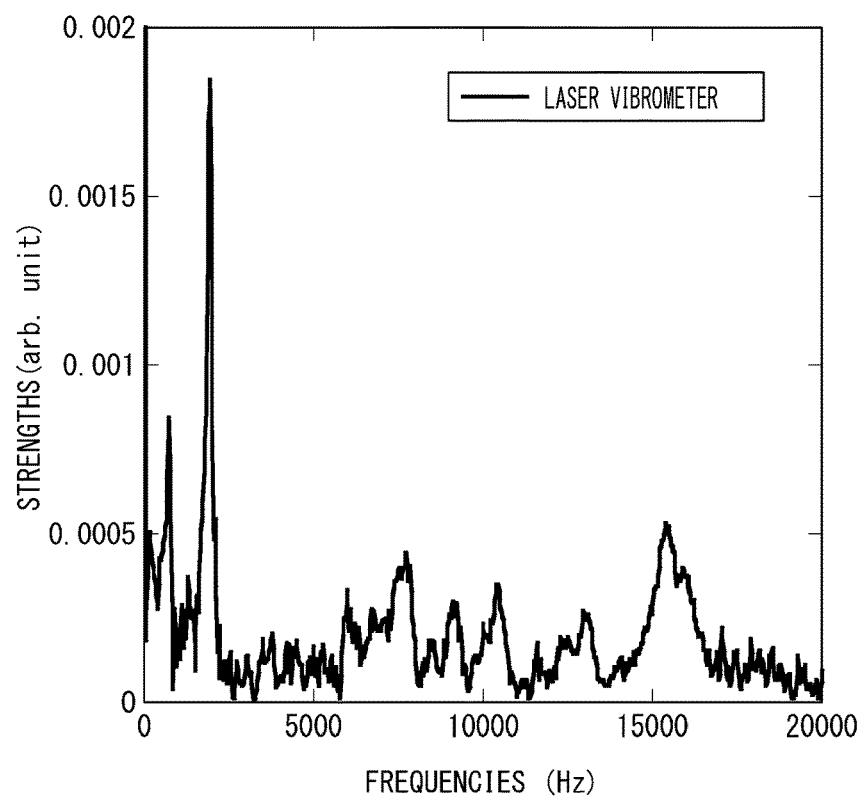
FIG. 7B is a view illustrating another vibration evaluation result in the example (Example 1).

FIGS. 7A and 7B are views illustrating vibration evaluation results in the example (Example 1). FIG. 7A shows a result of vibration induced in the implant 450 measured by the acceleration sensor 440. In FIG. 7A, the horizontal axis indicates frequencies (Hz), and the vertical axis indicates strengths (V).

FIG. 7B shows a result of vibration induced in the implant 450 measured by the second laser system 410. In FIG. 7B, the horizontal axis indicates frequencies (Hz), and the vertical axis indicates strengths (arb. unit).

According to FIGS. 7A and 7B, the frequency spectrum of the number of vibrations and a vibration strength measured by the acceleration sensor 440 and the frequency spectrum of the number of vibrations and a vibration strength measured by the second laser system 410 are similar to each other. Therefore, it can be seen that the second laser system 410 can be used for obtaining the number of vibrations and a vibration strength of the implant 450.

Figure 8:
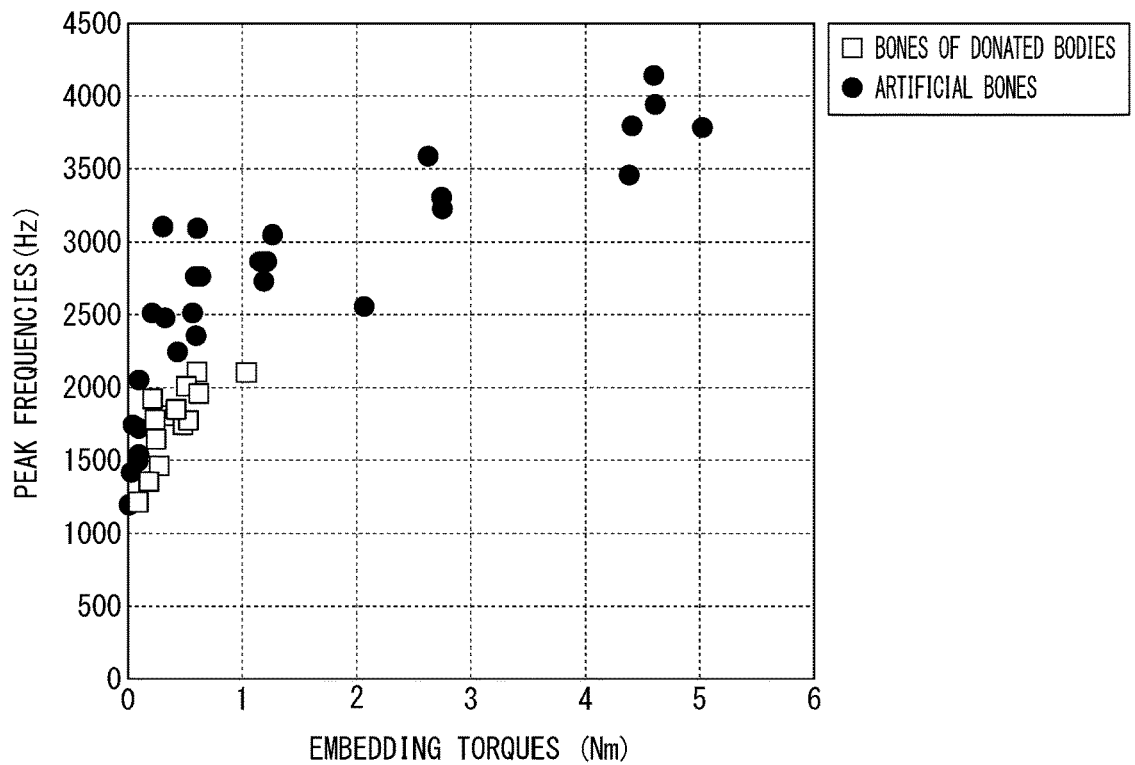
FIG. 8 is a view illustrating an example of association between peak frequencies and embedding torques.

FIG. 8 is a view illustrating an example of association between embedding torques and peak frequencies. In FIG. 8, the horizontal axis indicates embedding torques (Nm), and the vertical axis indicates peak frequencies (Hz). As an example of the evaluation target 50, FIG. 8 illustrates a case in which the implant 450 is installed in the artificial bone 460 and measurement is performed and a case in which the implant 450 is installed in a bone of an unfrozen fresh cadaver (which will hereinafter be referred to as "a bone of a donated body") and measurement is performed. According to FIG. 8, even when a bone of a donated body most similar to a living body is used, it can be seen that there is a correlation between the embedding torque and the peak frequency similar to the case in which the artificial bone 460 is used. Therefore, an embedding torque of the implant 450 can be estimated from the peak frequency.

Figure 9:
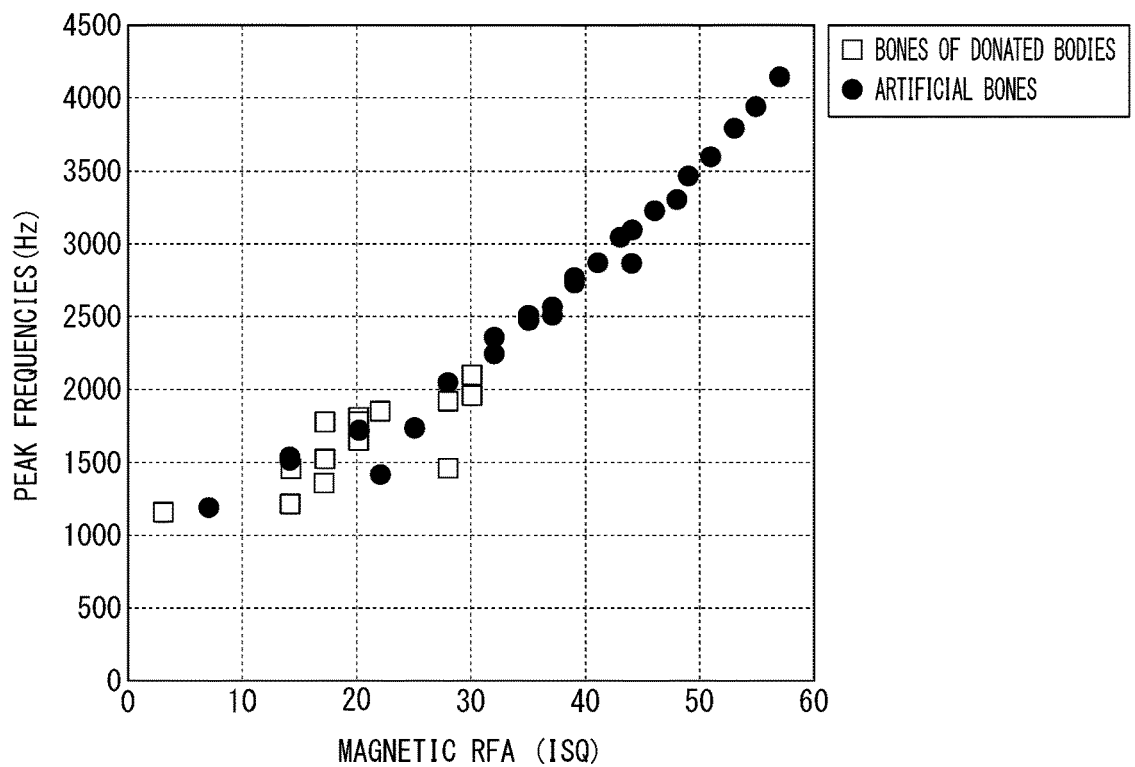
FIG. 9 is a view illustrating an example of association between peak frequencies and measurement values from magnetic RFA.

FIG. 9 is a view illustrating an example of association between magnetic RFA measurement values (implant stability quotients (ISQ)) and peak frequencies. In FIG. 9, the horizontal axis indicates magnetic RFA measurement values (ISQ) measured by magnetic resonance frequency analysis (RFA), and the vertical axis indicates peak frequencies (Hz). Here, it is difficult to adapt magnetic RFA to orthopedic implants which are installed deep inside a body, but magnetic RFA is a technique which has already been clinically introduced in dental implants. The unit ISQ is an example of a value used when magnetic RFA is clinically introduced in the field of dentistry, and it denotes that the larger this value, the higher the installation strength of an implant. As an example of the evaluation target 50, FIG. 9 illustrates a case in which the implant 450 is installed in the artificial bone 460 and measurement is performed and a case in which the implant 450 is installed in a bone of a donated body and measurement is performed. According to FIG. 9, it can be seen that there is a correlation between the magnetic RFA measurement value and the peak frequency. Therefore, a magnetic RFA measurement value of the implant 450 can be estimated from the peak frequency.

Figure 10:
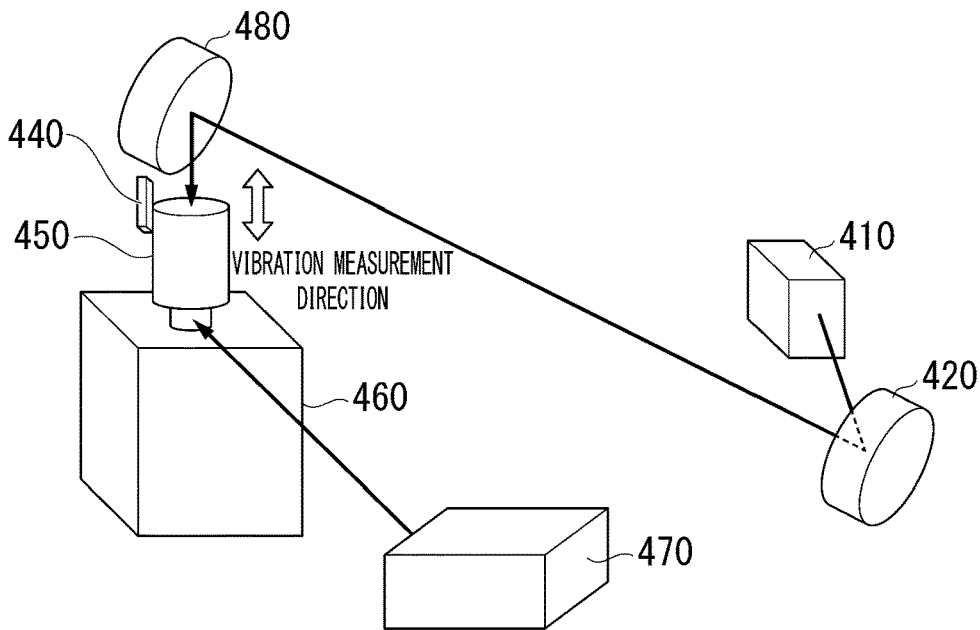
FIG. 10 is a view illustrating a vibration evaluation system in an example (Example 2).

FIG. 10 is a view illustrating a vibration evaluation system in an example (Example 2).

The vibration evaluation system includes the first laser system 470, the second laser system 410, the first reflector 420, the acceleration sensor 440, the implant 450, the artificial bone 460, and a second reflector 480. This vibration evaluation system differs from the vibration evaluation system illustrated in FIG. 6 in that the second reflector 480 is included.

Similar to FIG. 6, the vibration evaluation system vibrates a plurality of implants fixed to artificial bones at different embedding torques by irradiating each of the implants with the laser beam A. Then, the vibration evaluation system obtains frequency spectrums of the number of vibrations and vibration strengths of the vibrated implants and acquires the peak frequencies from the obtained frequency spectrums. Then, the vibration evaluation system associates the acquired peak frequencies and the embedding torques with each other.

The implant 450 is embedded in the artificial bone 460. The first laser system 470 generates the laser beam A for inducing vibration in the implant 450 and irradiates the root of the implant 450 with the generated laser beam A. The implant 450 vibrates when the root of the implant 450 is irradiated with the laser beam A. Specifically, an example of the first laser system 470 is a Nd:YAG laser. Irradiation energy of the laser beam A generated by the first laser system 470 may be set suitably within a range of 10 mJ to 30 mJ. Typically, it may be within a range of 15 mJ to 25 mJ. In addition, a repetitive frequency of the laser is within a range of 5 Hz to 15 Hz. The average number of instances of spectra is within a range of 100 times to 150 times.

The second laser system 410 generates the laser beam B1 for detecting vibration induced in the implant 450 and outputs the generated laser beam B1. The laser beam B1 output by the second laser system 410 is reflected by the first reflector 420, the laser beam B1 reflected by the first reflector 420 is reflected by the second reflector 480, and the head portion of the implant 450 is irradiated with the laser beam B1 reflected by the second reflector 480.

The direction of the first reflector 420 is adjusted such that the laser beam B1 output by the second laser system 410 is reflected to the second reflector 480. The direction of the second reflector 480 is adjusted such that the laser beam B1 reflected by the first reflector 420 is reflected to the head portion of the implant 450. The distance between the first reflector 420 and the second reflector 480 is approximately 1 m.

The implant 450 reflects the irradiation laser beam B1 from the second reflector 480. The laser beam B2 reflected by the implant 450 is reflected by the second reflector 480, the laser beam B2 reflected by the second reflector 480 is reflected by the first reflector 420, and the laser beam B2 reflected by the first reflector 420 is input to the second laser system 410. The vibration evaluation system illustrated in FIG. 10 mainly detects vibration in a direction in which the implant 450 is embedded in the artificial bone 460. An example of the second laser system 410 is a laser Doppler vibrometer, and an output thereof is within a range of 0.5 mW to 1.5 mW.

The acceleration sensor 440 is attached to the head portion of the implant 450 and detects vibration induced in the implant 450.

In this case as well, similar to FIGS. 7A and 7B, the frequency spectrum of vibration measured by the acceleration sensor 440 and the frequency spectrum of vibration measured by the second laser system 410 are similar to each other. Therefore, it can be seen that the second laser system 410 can be used for obtaining the number of vibrations and a vibration strength of the implant 450.

The vibration evaluation system acquires the peak frequency at which the vibration strength peaks and causes the acquired peak frequency and the embedding torque to be associated with each other based on the frequency spectrum of vibration.

Figure 11:
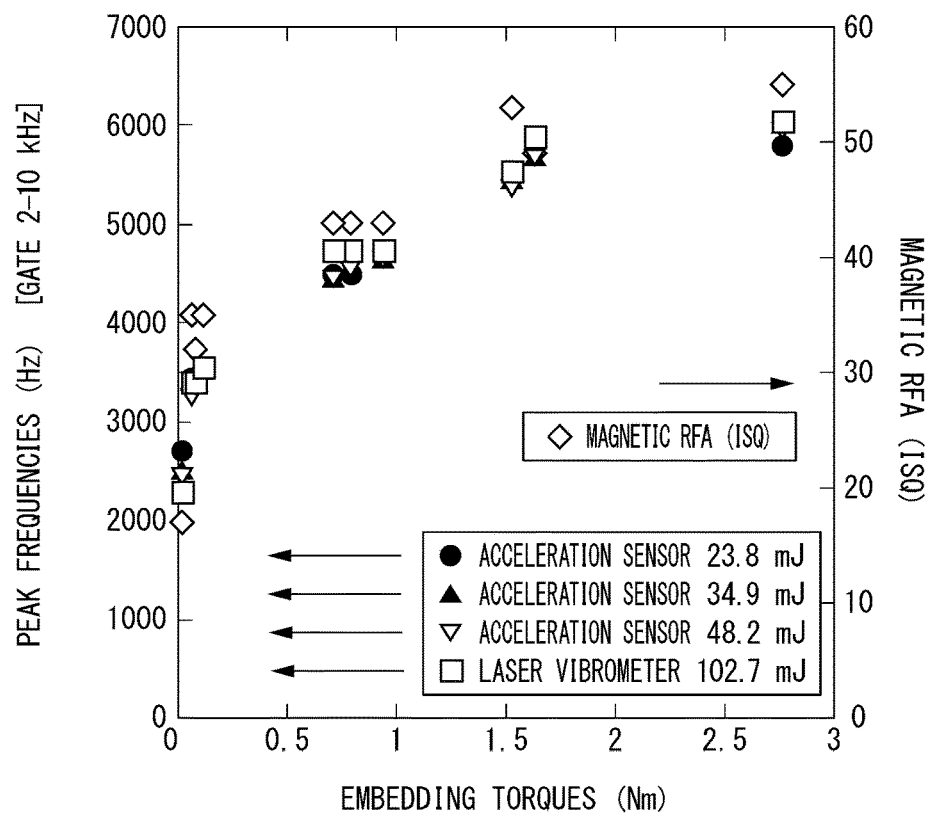
FIG. 11 is a view illustrating an example of association between peak frequencies and embedding torques.

FIG. 11 is a view illustrating an example of association between embedding torques and peak frequencies. In FIG. 11, the horizontal axis indicates embedding torques (Nm), and the vertical axis indicates peak frequencies (Hz). FIG. 11 illustrates magnetic RFA measurement values (ISQ) measured by magnetic resonance frequency analysis in addition to peak frequencies acquired from the frequency spectrums of vibration measured by the acceleration sensor 440 and peak frequencies acquired from the frequency spectrums of vibration measured by the second laser system 410 (laser vibrometer). According to FIG. 11, it can be seen that there is a correlation between the embedding torque and the peak frequency regardless of a measurement technique. Therefore, an embedding torque of the implant 450 can be estimated from the peak frequency.

Figure 12A:
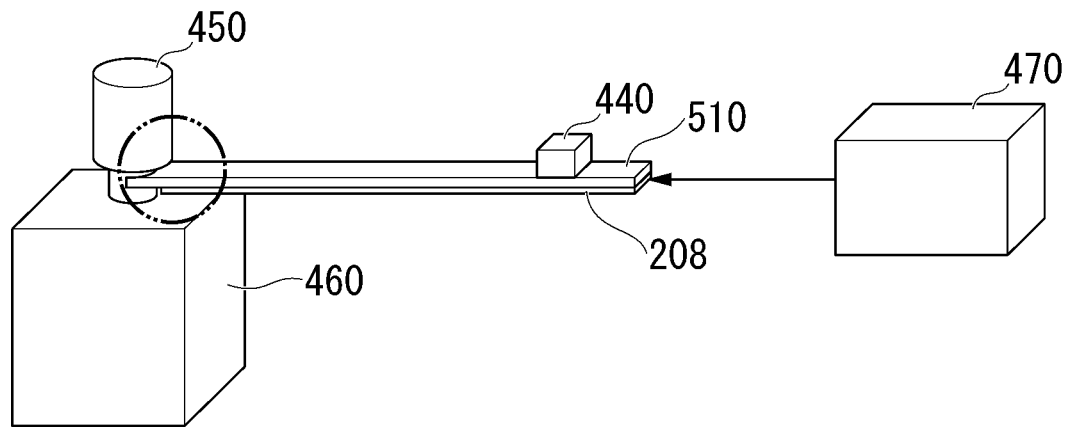
FIG. 12A is a view illustrating a vibration evaluation system in an example (Example 3-1).

FIG. 12A is a view illustrating a vibration evaluation system in an example (Example 3-1).

Figure 12B:
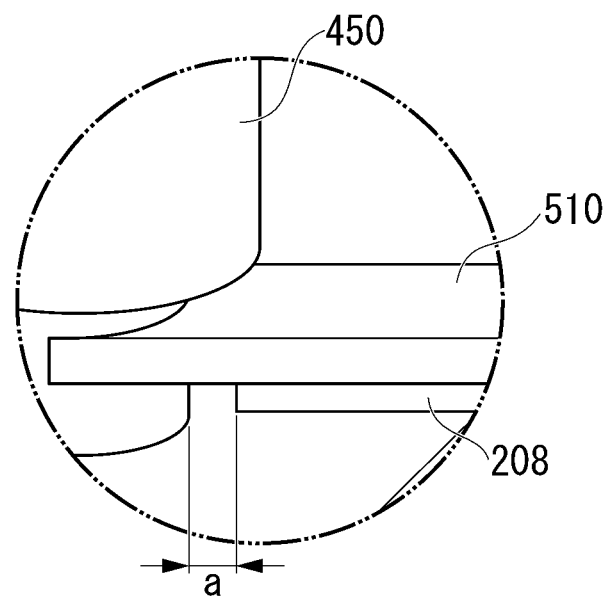
FIG. 12B is a partial enlarged view of the vibration evaluation system in the example (Example 3-1).

FIG. 12B is a partial enlarged view of the vibration evaluation system in the example (Example 3-1).

Figure 12C:
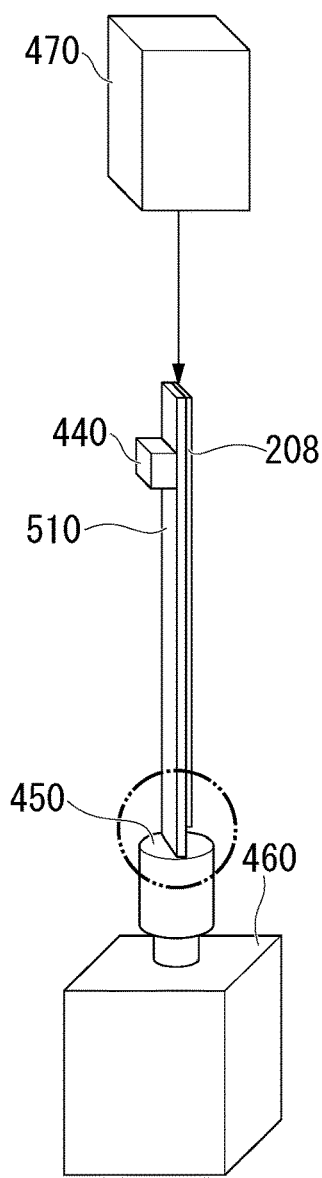
FIG. 12C is a view illustrating a vibration evaluation system in an example (Example 3-2).

FIG. 12C is a view illustrating a vibration evaluation system in an example (Example 3-2).

Figure 12D:
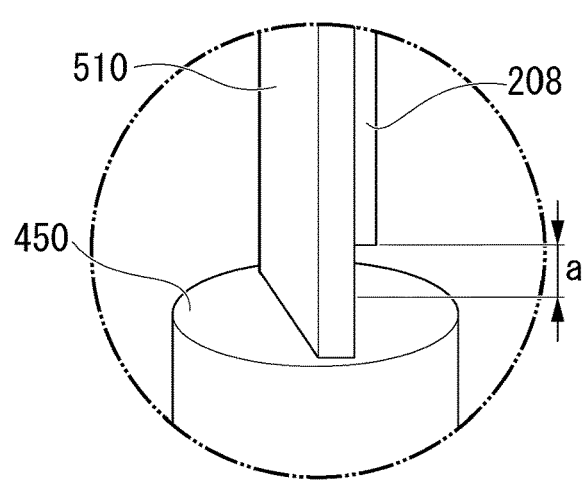
FIG. 12D is a partial enlarged view of the vibration evaluation system in the example (Example 3-2).

FIG. 12D is a partial enlarged view of the vibration evaluation system in the example (Example 3-2).

The vibration evaluation system includes the first laser system 470, the acceleration sensor 440, the implant 450, the artificial bone 460, and a probe 510. This vibration evaluation system differs from the vibration evaluation system illustrated in FIG. 10 in that the probe 510 in which the acceleration sensor 440 is installed is brought into contact with the implant 450 and measuring vibration of the implant 450.

In FIG. 12A, one end of the probe 510 comes into contact with a root part of the implant 450. In FIG. 12C, one end of the probe 510 comes into contact with the head portion of the implant 450.

An example of the probe 510 is a stainless steel rod, and one end thereof comes into contact with the implant 450. In addition, the probe 510 is provided with an optical fiber 208 of which a tip is shortened slightly due to a length thereof being shorter than the probe 510 such that one end thereof does not come into contact with the implant 450.

The optical fiber 208 allows light output by the first laser system 470 to be transmitted therethrough. The implant 450 is vibrated when the implant 450 is irradiated with laser light from the optical fiber 208. Vibration of the implant 450 induced by the laser light output from the optical fiber 208 is transferred through the probe 510 and is detected by the acceleration sensor 440.

Since the energy density of laser light output from the optical fiber 208 decreases rapidly due to diffractive expansion occurring immediately after the laser light is output, it is desired that the optical fiber 208 be closer to the implant 450. As an example, it is desired that the optical fiber 208 be set at a distance shorter than a tip of the probe 510 within a range of approximately 0.1 mm to 2 mm. The enlarged views illustrated in FIGS. 12B and 12D are examples when a distance of approximately 1 mm is set as a distance a between the tip of the probe 510 and the tip of the optical fiber 208. However, the distance is not limited thereto when a condensing optical element such as a microlens is mounted at the tip of the optical fiber 208, and a focal distance of the condensing optical element is set at an optimum shortened distance (for example, within a range of 10 mm to 50 mm).

Figure 13:
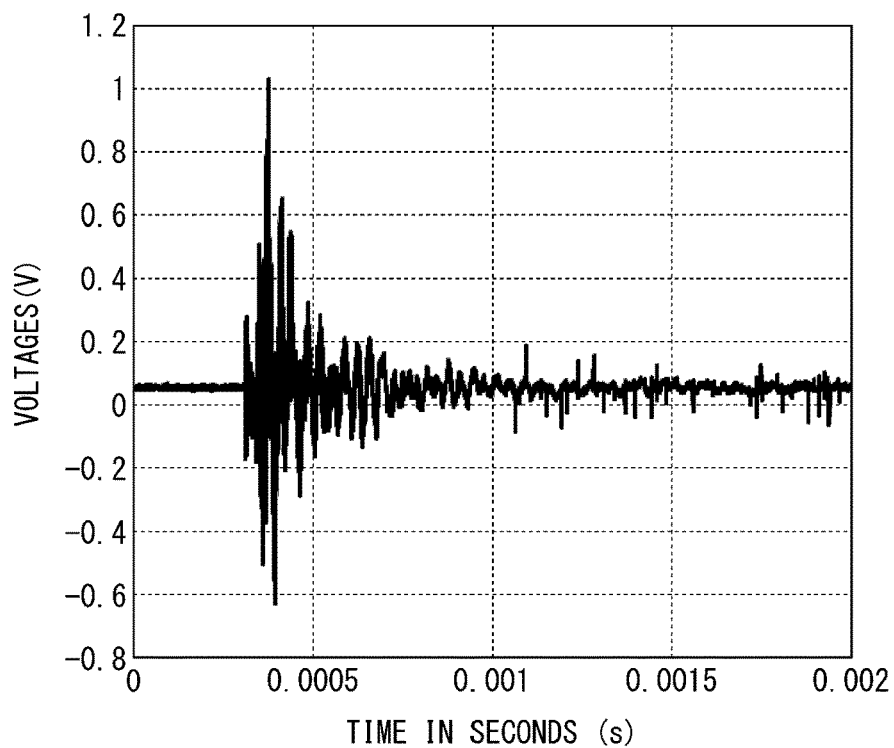
FIG. 13 is a view illustrating a vibration evaluation result in an example (Example 3).

FIG. 13 is a view illustrating a vibration evaluation result in an example (Example 3). In FIG. 13, the horizontal axis indicates time in seconds(s), and the vertical axis indicates voltages (V).

According to FIG. 13, vibration of the implant 450 detected by the acceleration sensor 440 can be indicated with a change in voltage. A vibration spectrum can be obtained by performing Fourier conversion of signals detected by the acceleration sensor 440.

In the example of the vibration evaluation system illustrated in FIG. 12, a case in which the probe 510 is a stainless steel rod has been described, but it is not limited to this example. For example, the material of the probe 510 may be any material such as a metal material or a resin material. In addition, the cross section of the probe 510 is not limited to a circular shape and may have a rectangular shape. In addition, the shape of the probe 510 is not limited to a linear shape and may be a curved shape. In addition, the installation position of the acceleration sensor 440 is not limited to a side surface of the probe 510 and may be an end portion.

In addition, a method of detecting vibration of the implant 450 is not limited to detection using the acceleration sensor 440. For example, the second laser system 410 generating a laser beam for detecting vibration induced in the implant 450 is prepared, and the probe 510 is irradiated with a laser beam output by the prepared second laser system 410. A laser beam with which the probe 510 is irradiated is reflected by the probe 510, and the laser beam reflected by the probe 510 is input to the second laser system 410. An example of the second laser system 410 is a laser Doppler vibrometer.

In addition, vibration of the implant 450 transferred through the probe 510 is not limited to vibration induced by an irradiation laser beam.

In the first embodiment described above, a case in which the implant installation strength evaluation device 100a and the second laser system 250 are connected to each other through the cable 202 has been described, but it is not limited thereto. For example, the implant installation strength evaluation device 100a and the second laser system 250 may be connected to each other by radio.

In the first embodiment described above, a case in which the implant installation strength evaluation device 100a, the first laser system 200, and the second laser system 250 are separate devices has been described, but they are not limited to this example. For example, the first laser system 200 and the second laser system 250 may be included in the implant installation strength evaluation device 100a.

In the first embodiment described above, a case in which an embedding torque is applied has been described as an example of the information indicating the index of the installation strength of the evaluation target 50, but it is not limited thereto. For example, information other than an embedding torque may be used or information in which an embedding torque and information other than an embedding torque are combined may be used as the information indicating the index of the installation strength of the evaluation target 50.

In the first embodiment described above, a case in which a peak frequency at which a vibration strength peaks is acquired from a frequency spectrum has been described, but it is not limited thereto. For example, a frequency corresponding to a predetermined vibration strength may be acquired from a frequency spectrum.

In the first embodiment described above, a case in which the implant installation strength evaluation device 100a determines whether or not an embedding torque is included within a range set in advance so that the embedding torque is considered appropriate when it is included within the range and the embedding torque is considered inappropriate when it is not included within the range has been described, but it is not limited to this example. For example, embedding torques may be classified into three or more groups depending on values of the embedding torques and states of the classified embedding torques may be indicated.

In the first embodiment described above, a case in which an installation strength of an implant for orthopedics is evaluated when the implant is installed in a human bone has been described, but it is not limited to this example. For example, the embodiment can also be applied to a case in which an installation strength of an artificial tooth root is evaluated when the artificial tooth root is embedded in a jawbone in the field of dentistry.

According to at least the implant installation strength evaluation system of the first embodiment, the implant installation strength evaluation system vibrates an evaluation target when the evaluation target is irradiated with the laser beam A. Due to such a constitution, an evaluation target can be vibrated in a non-contact manner. For example, when a resonance frequency is acquired by vibrating an implant using a magnetic force in RFA, there is a need to install a jig having a magnet in the implant. Therefore, it is difficult to apply the method to orthopedic implants which are sometimes installed deep inside a body.

The implant installation strength evaluation system irradiates a vibrated evaluation target with the laser beam B1 and derives a frequency spectrum of vibration of the evaluation target based on the laser beam B2 that is the reflected laser beam B1 from the evaluation target. Due to such a constitution, a frequency spectrum of vibration of an evaluation target can be derived in a non-contact manner without attaching a device such as an acceleration sensor to the evaluation target.

The implant installation strength evaluation system acquires a peak frequency from a derived frequency spectrum and acquires an embedding torque associated with the acquired peak frequency. Due to such a constitution, an embedding torque reflecting a gap between an evaluation target and a base (bone) fixing the evaluation target and a strength of the base can be acquired. Then, an evaluation result indicating whether or not the installation strength of the evaluation target 50 is appropriate can be acquired based on the embedding torque.

Recently, implant operations for fracture of the limbs or the spine are increasing rapidly due to increasing osteoporotic patients. However, the installation strength of an implant decreases in the limbs or the spine. This results in a problem that the purpose of a surgical operation cannot be achieved due to looseness of an implant and a reoperation is required.

However, in recent years, evaluation items for an installation strength of an implant are still limited to old-fashioned techniques, such as an evulsion force and the embedding torque, and it is difficult to say that these techniques actually reflect forces applied to an implant inside a body. There is no correlation between measurement results and the incidence of looseness. In addition, these techniques are invasive and they can be executed only once. There is significant deviation in a subject and between subjects.

The implant installation strength evaluation system of the first embodiment is non-invasive so that it can be performed repeatedly, and deviation in a subject and between subjects can be reduced. In the implant installation strength evaluation system of the first embodiment, since there is no need to install a jig having a magnet in an implant, the installation strength of the implant can be evaluated during a surgical operation. Until now, selection or the installation strength of an implant has had to rely on the judgment of an operator, but the selection or the installation strength of an implant can be objective. Therefore, the success rate of a surgical operation can be improved without relying on the skill of an operator.

Second Embodiment (Implant Installation Strength Evaluation System)

FIG. 1 can be applied as an example of an implant installation strength evaluation system of a second embodiment.

The implant installation strength evaluation system vibrates the evaluation target 50, such as an implant, by irradiating it with a laser beam. In the second embodiment, an artificial joint is postulated as an example of the evaluation target 50.

The implant installation strength evaluation system acquires time series data of vibration with respect to each vibration frequency of the vibrated evaluation target 50 and derives a frequency spectrum of vibration based on the time series data of vibration with respect to each of the acquired vibration frequencies. The implant installation strength evaluation system acquires information indicating an index of an installation strength of the evaluation target 50 by analyzing the derived frequency spectrum. In the second embodiment, description will be continued regarding a case in which a pulling force is applied as an example of the information indicating the index of the installation strength of the evaluation target 50. The implant installation strength evaluation system acquires an evaluation result indicating whether or not the installation strength of the evaluation target 50 is appropriate based on the derived pulling force of the evaluation target 50.

The implant installation strength evaluation system includes an implant installation strength evaluation device 100b, the first laser system 200, the second laser system 250, and the irradiation head 300. This implant installation strength evaluation system differs from the implant installation strength evaluation system of the first embodiment in that the implant installation strength evaluation device 100b is included in place of the implant installation strength evaluation device 100a.

The implant installation strength evaluation device 100b acquires the information indicating the number of vibrations and a vibration strength output by the second laser system 250. The implant installation strength evaluation device 100a acquires a frequency spectrum in which a frequency and a vibration strength are associated with each other by performing Fourier conversion of the time series data of the number of vibrations and vibration strengths based on the acquired information indicating the number of vibrations and a vibration strength.

The implant installation strength evaluation device 100b acquires a peak frequency at which the number of vibrations peaks from the acquired frequency spectrum. The implant installation strength evaluation device 100b acquires a pulling force based on the acquired peak frequency. Here, a pulling force indicates a force acting when an artificial joint cup is detached from a bone (an artificial bone or a human bone) in a case in which an installation rod is attached to the artificial joint cup attached to the bone and the installation rod is pulled. Here, a pulling force reflects a gap between a bone and the artificial joint cup, and the strength of a base. There is concern that if the pulling force is excessively low, fixing in an initial stage may become weak, and if the pulling force is excessively high, avascular bone necrosis may be caused around an artificial joint cup. Therefore, it is possible to evaluate whether or not the installation strength of an implant is appropriate by monitoring the pulling force.

(Evaluation Target)

An example of the evaluation target 50 will be described.

Figure 14:
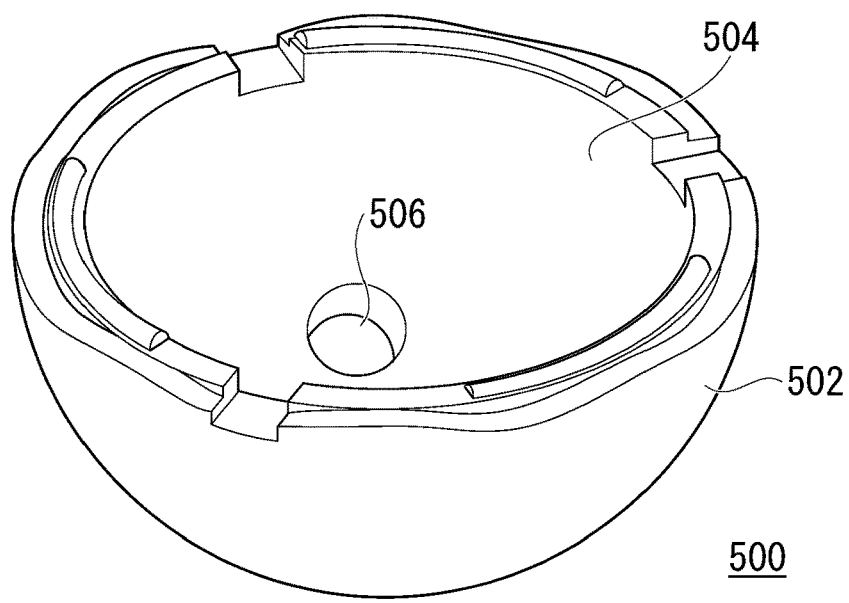
FIG. 14 is a view illustrating an example of an evaluation target of a second embodiment.

FIG. 14 is a view illustrating an example of an evaluation target of a second embodiment. Here, an artificial joint cup 500 is illustrated as an example of the evaluation target 50. The artificial joint cup 500 may include a metal or a metal alloy, such as a titanium or a titanium alloy. The artificial joint cup 500 has an outer surface 502. The outer surface 502 has a convex shape such that it can approximate the shape of a surgical operation site when it is stored appropriately. The outer surface 502 is coated with a porous material for improving joining of the artificial joint cup 500 to a surgical operation site. A porous material coating may include a titanium or a titanium alloy.

The artificial joint cup 500 may also be fixed to a surgical operation site using an appropriate cement for a surgical operation or for bones. An inner surface 504 of the artificial joint cup 500 has a concave shape and may be manufactured of the same material as the outer surface 502.

The artificial joint cup 500 further includes a hole 506 through which one or more installation rods such as screws can move forward into a pelvic bone through the artificial joint cup 500. Each of the installation rods can support fixing of the artificial joint cup 500 at a desired position inside the pelvis by providing a scaffold inside the pelvic bone.

A predetermined position on the inner surface 504 of the artificial joint cup 500 is irradiated with the laser beam A generated by the first laser system 200 from the irradiation head 300. Moreover, a predetermined position on the inner surface 504 of the artificial joint cup 500 is irradiated with the laser beam B1 generated by the second laser system 250 from the irradiation head 300.

(Implant Installation Strength Evaluation Device)

Figures 15, 16:
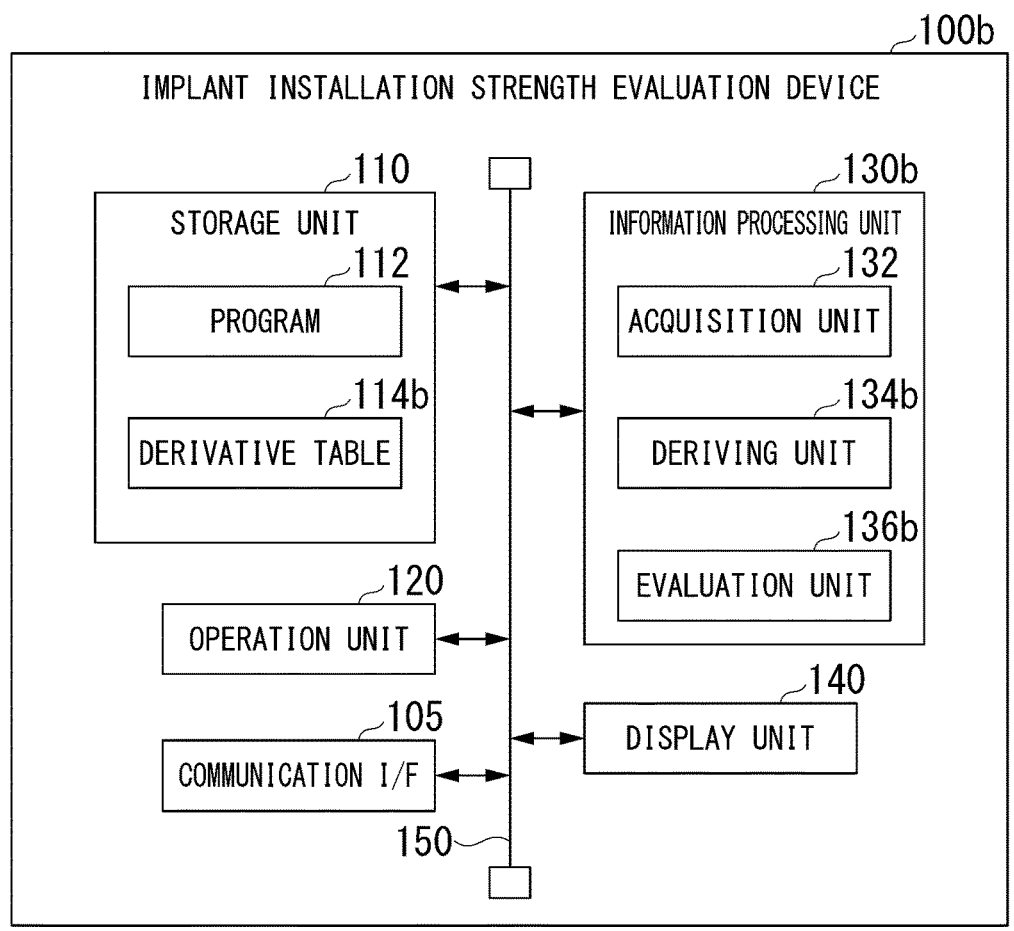
FIG. 15 is a view illustrating an example of an implant installation strength evaluation device of the second embodiment.
FIG. 16 is a view illustrating an example of a derivative table.

FIG. 15 is a view illustrating an example of the implant installation strength evaluation device 100b of the second embodiment.

The implant installation strength evaluation device 100b includes the communication I/F 105, the storage unit 110, the operation unit 120, an information processing unit 130b, the display unit 140, and the bus line 150 for an address bus, a data bus, and the like for electrically connecting each of the constituent elements as illustrated in FIG. 11.

For example, the storage unit 110 is realized by a RAM, a ROM, an HDD, a flash memory, a hybrid storage device in which a plurality of elements of these are combined, or the like. The storage unit 110 stores the program 112 executed by the information processing unit 130b, and a derivative table 114b.

(Derivative Table)

FIG. 16 is a view illustrating an example of a derivative table. The derivative table 114b is a table in which peak frequencies and pulling forces are associated with each other. The peak frequency is a peak frequency acquired from the frequency spectrum of vibration of the evaluation target 50 when the evaluation target 50 is vibrated a laser beam. The pulling force is a pulling force which is associated with the peak frequency of the vibrated evaluation target 50. Association between a peak frequency and a pulling force of the evaluation target 50 will be described below. In the example illustrated in FIG. 16, the peak frequency "a1" and a pulling force "c1" are stored in association with each other.

Returning to FIG. 15, description will be continued. For example, the entirety or a part of the information processing unit 130b is a software functional unit realized by a processor such as a CPU executing the program 112 stored in the storage unit 110. The entirety or a part of the information processing unit 130b may be realized by hardware such as an LSI, an ASIC, or an FPGA or may be realized by a combination of a software functional unit and hardware.

For example, the information processing unit 130b includes the acquisition unit 132, a deriving unit 134b, and an evaluation unit 136b.

The deriving unit 134b derives a frequency spectrum of vibration with respect to each of the vibration frequencies of the evaluation target 50 based on the information indicating the number of vibrations and a vibration strength of the evaluation target 50 output by the acquisition unit 132. The deriving unit 134b acquires a peak frequency at which the vibration strength peaks in the derived frequency spectrum. Specifically, when x indicates the frequency, the deriving unit 134b has a function f(x) expressing the frequency spectrum. The deriving unit 134b designates a frequency range of x=1 kHz to 20 kHz and more preferably designates a frequency range of x=2 kHz to 10 kHz because the component of the number of high-frequency vibrations is invariable.

The deriving unit 134b obtains x satisfying $df(x)/dx=0$ in which the function f(x) is differentiated by x and $d^2f(x)/dx^2<0$ in which the function f(x) is differentiated twice by x. The deriving unit 134b has f(n) (n=0, 1, 2, and so on) in order from x having a smaller value. The deriving unit 134b acquires the smallest f(n) satisfying f(n)>max f(x)×C (max f(x) indicates the largest value of f(x), and C indicates an arbitrary constant for determining a threshold).

The deriving unit 134b acquires the pulling force associated with the acquired peak frequency from association between peak frequencies and pulling forces included in the derivative table 114b stored in the storage unit 110. The deriving unit 134b outputs information indicating the acquired pulling force to the evaluation unit 136b.

The evaluation unit 136b acquires the information indicating the pulling force output by the deriving unit 134b. The evaluation unit 136b determines whether or not the acquired pulling force is within a range set in advance. When the acquired pulling force is included within the range set in advance, the evaluation unit 136b acquires an evaluation result in which the pulling force is appropriate. When the acquired pulling force is not included within the range set in advance, the evaluation unit 136b acquires an evaluation result in which the pulling force is inappropriate. The evaluation unit 136b outputs the evaluation result of the pulling force to the display unit 140.

The display unit 140 acquires the evaluation result of the pulling force output by the evaluation unit 136b. The display unit 140 displays the acquired evaluation result of the pulling force.

(Operation of Implant Installation Strength Evaluation Device)

Figure 17:
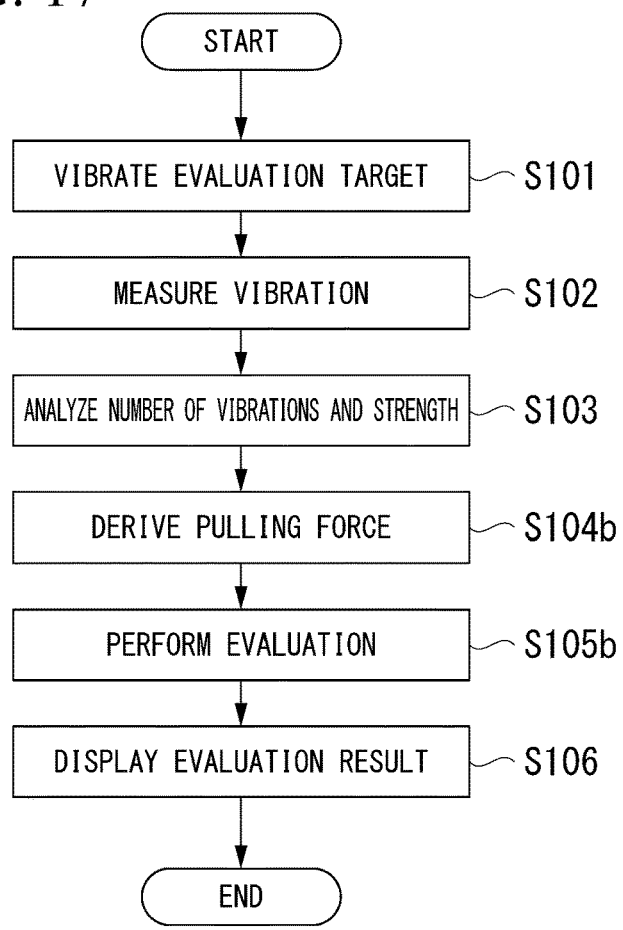
FIG. 17 is a view illustrating an example of operation of the implant installation strength evaluation device of the second embodiment.

FIG. 17 is a view illustrating an example of operation of the implant installation strength evaluation device of the second embodiment. Steps S101 to S103 and S106 have already been described with reference to FIG. 5, and therefore description herein will be omitted.

(Step S104b)

The deriving unit 134b of the implant installation strength evaluation device 100b acquires the pulling force associated with the acquired peak frequency from the derivative table 114b stored in the storage unit 110. The deriving unit 134b outputs the information indicating the acquired pulling force to the evaluation unit 136b.

(Step S105b)

The evaluation unit 136b of the implant installation strength evaluation device 100b acquires the information indicating the pulling force output by the deriving unit 134b. When the pulling force is included within the range set in advance, the evaluation unit 136b acquires a determination result in which the pulling force is appropriate based on the information indicating the acquired pulling force. In this case, the installation strength of the evaluation target 50 is evaluated as being appropriate. When the acquired pulling force is not included within the range set in advance, the evaluation unit 136b acquires a determination result in which the pulling force is inappropriate. In this case, the installation strength of the evaluation target 50 is evaluated as being inappropriate. The evaluation unit 136b outputs the evaluation result of the installation strength of the evaluation target 50 to the display unit 140.

According to operation of the implant installation strength evaluation device illustrated in FIG. 17, the implant installation strength evaluation device 100b acquires a peak frequency from the frequency spectrum of vibration of the vibrated evaluation target 50. The implant installation strength evaluation device 100a acquires a pulling force associated with the acquired peak frequency from association between peak frequencies and pulling forces. The implant installation strength evaluation device 100b acquires an evaluation result indicating whether or not the installation strength of the evaluation target 50 is appropriate from the acquired pulling force.

(Example of Derived Association Between Peak Frequencies and Pulling Forces)

Here, an example of derived association between peak frequencies and pulling forces will be described.

Figure 18:
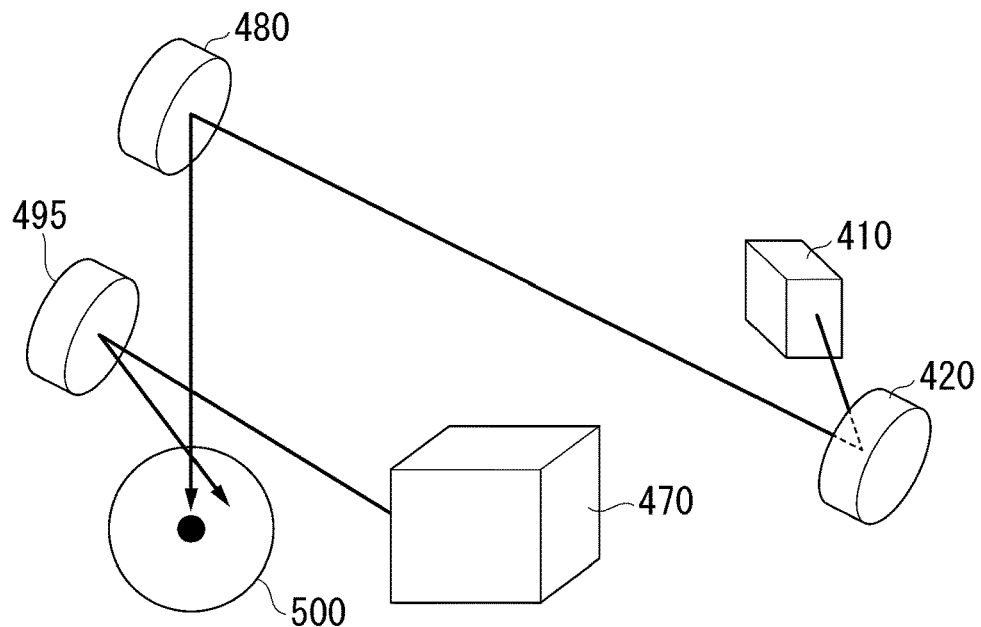
FIG. 18 is a view illustrating a vibration evaluation system in an example (Example 4).

FIG. 18 is a view illustrating a vibration evaluation system in an example (Example 4). The peak frequencies and the pulling forces are associated with each other prior to the processing of the implant installation strength evaluation device 100b evaluating whether or not the installation strength of the evaluation target 50 is appropriate. Then, association between peak frequencies and pulling forces is stored in the derivative table 114b.

In the vibration evaluation system illustrated in FIG. 18, the artificial joint cups to which the installation rods are fixed with different forces are vibrated when each of the artificial joint cups 500 is irradiated with a laser beam. Then, the vibration evaluation system obtains frequency spectrums of vibration of the vibrated artificial joint cups and acquires peak frequencies from the obtained frequency spectrums. Then, the vibration evaluation system associates the acquired peak frequencies and the pulling forces with each other.

The vibration evaluation system includes the first laser system 470, the second laser system 410, the first reflector 420, the second reflector 480, a third reflector 495, and the artificial joint cup 500.

The installation rod is attached to a bolt hole at the bottom of the artificial joint cup 500.

The first laser system 470 generates the laser beam A for inducing vibration in the artificial joint cup 500 and outputs the generated laser beam A. The laser beam A output by the first laser system 470 is reflected by the third reflector 495, and the artificial joint cup 500 is irradiated with the laser beam A reflected by the third reflector 495. The artificial joint cup 500 vibrates when the artificial joint cup 500 is irradiated with the laser beam A.

The direction of the third reflector 495 is adjusted such that a predetermined position on the inner surface 504 of the artificial joint cup 500 is irradiated with the laser beam A output by the first laser system 470. Specifically, an example of the first laser system 470 is a Nd:YAG laser. Irradiation energy of the laser beam generated by the first laser system 470 may be set suitably within a range of 20 mJ to 80 mJ, for example. Typically, it may be within a range of 40 mJ to 60 mJ. In addition, a repetitive frequency of the laser is within a range of 5 Hz to 15 Hz.

The second laser system 410 generates the laser beam B1 for detecting vibration induced in the artificial joint cup 500 and outputs the generated laser beam B1. The laser beam B1 output by the second laser system 410 is reflected by the first reflector 420, the laser beam B1 reflected by the first reflector 420 is reflected by the second reflector 480, and a predetermined position on the inner surface 504 of the artificial joint cup 500 is irradiated with the laser beam reflected by the second reflector 480.

The direction of the first reflector 420 is adjusted such that the second reflector 480 is irradiated with the laser beam B1 output by the second laser system 410. In addition, the direction of the second reflector 480 is adjusted such that a predetermined position on the inner surface 504 of the artificial joint cup 500 is irradiated with the laser beam B1 reflected by the first reflector 420. The distance between the first reflector 420 and the second reflector 480 is approximately 1 m.

The artificial joint cup 500 reflects the laser beam B1 reflected by the second reflector 480. The laser beam B2 reflected by the artificial joint cup 500 is reflected by the second reflector 480, the laser beam B2 reflected by the second reflector 480 is reflected by the first reflector 420, and the laser beam B2 reflected by the first reflector 420 is input to the second laser system 410.

Figure 19:
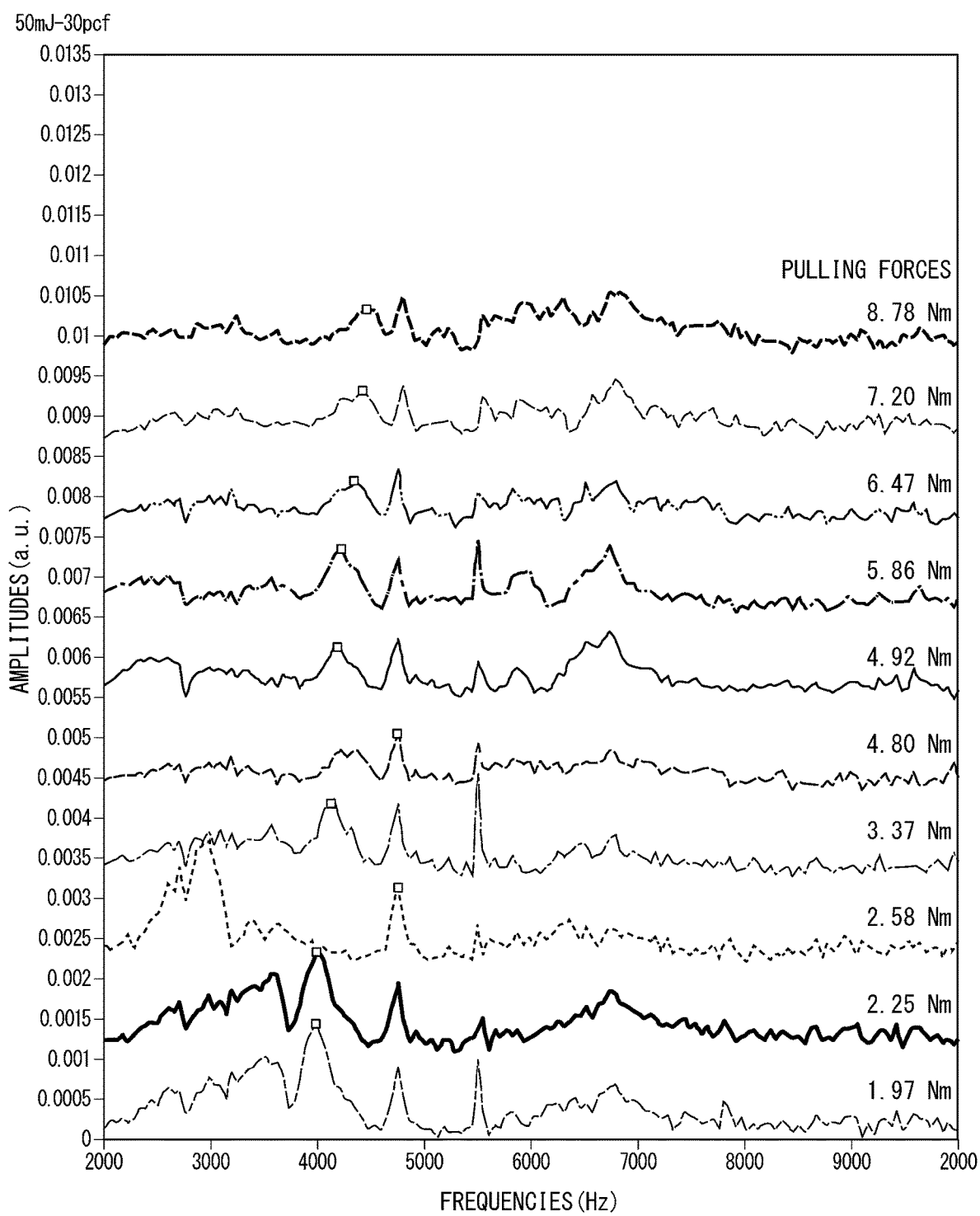
FIG. 19 is a view illustrating a vibration evaluation result in the example (Example 4).

FIG. 19 is a view illustrating a vibration evaluation result in the example (Example 4).

In FIG. 19, the horizontal axis indicates frequencies (Hz), and the vertical axis indicates amplitudes (arb. unit). FIG. 19 illustrates relationships between the frequencies and the amplitudes for each of the pulling forces of 1.97 Nm, 2.25 Nm, 2.58 Nm, 3.37 Nm, 4.80 Nm, 4.92 Nm, 5.86 Nm, 6.47 Nm, 7.20 Nm, and 8.78 Nm. Regardless of the pulling forces, similar waveforms are obtained. In addition, in FIG. 19, the "□" marks indicate respective peaks.

Figure 20:
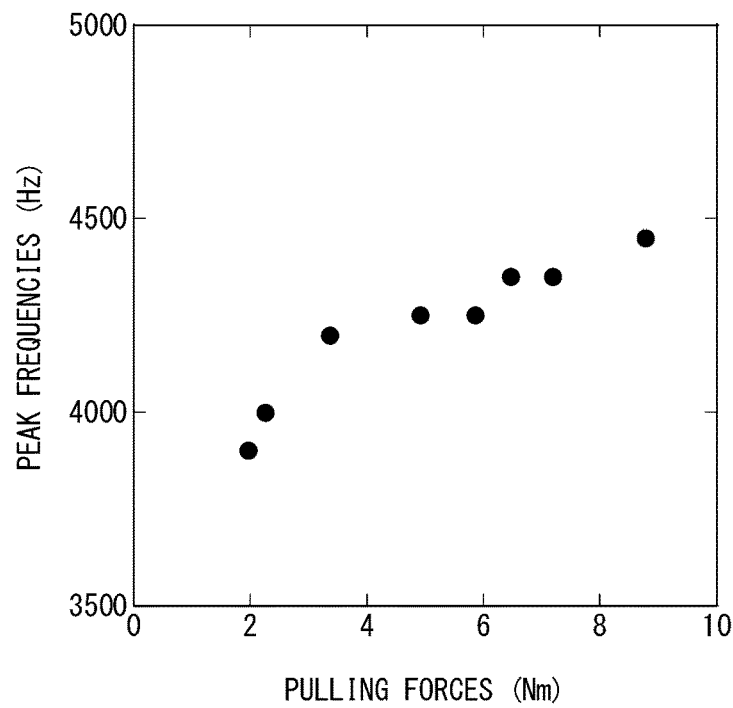
FIG. 20 is a view illustrating an example of association between peak frequencies and pulling forces.

FIG. 20 is a view illustrating an example of association between pulling forces and peak frequencies. In FIG. 20, the horizontal axis indicates pulling forces (Nm), and the vertical axis indicates peak frequencies (Hz). FIG. 20 illustrates the peak frequencies acquired from the frequency spectrum of vibration measured by the second laser system 410 (laser vibrometer). According to FIG. 20, it can be seen that there is a correlation between the pulling force and the peak frequency at which the vibration frequency peaks. Therefore, a pulling force for the installation rod attached to the bolt hole of the artificial joint cup can be acquired by acquiring the peak frequency.

Figure 21:
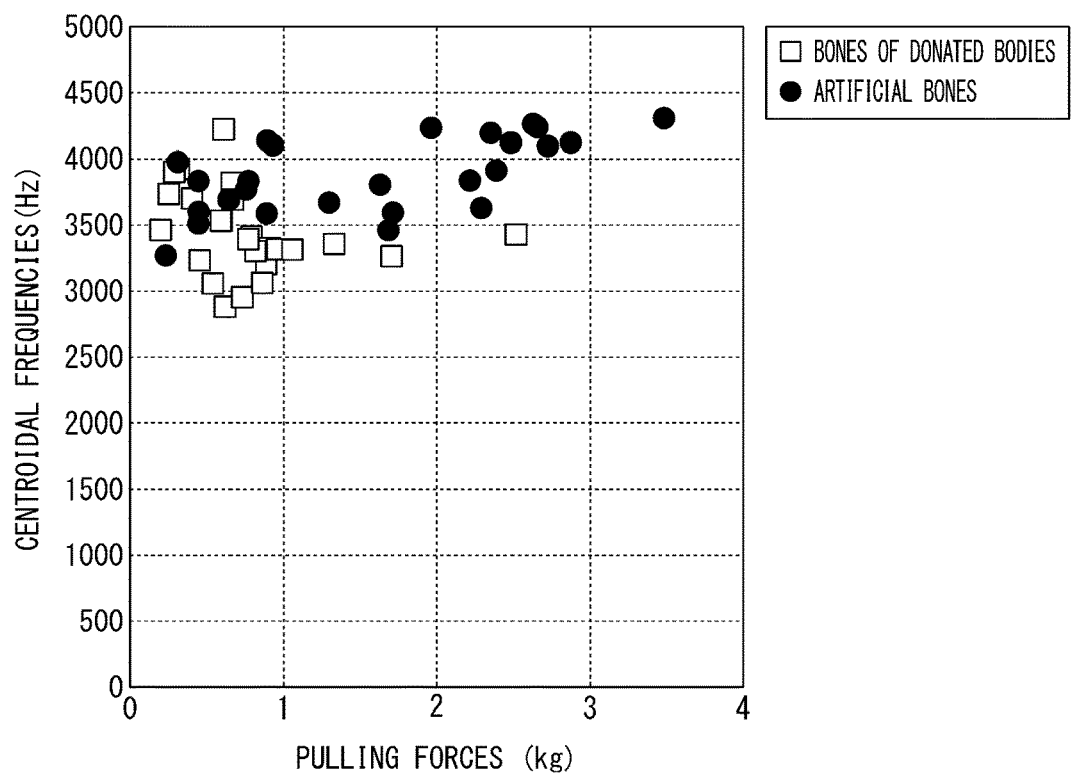
FIG. 21 is a view illustrating an example of association between centroidal frequencies and pulling forces.

FIG. 21 is a view illustrating an example of association between pulling forces and centroidal frequencies. In FIG. 21, the horizontal axis indicates pulling forces (kg), and the vertical axis indicates centroidal frequencies (Hz). FIG. 21 illustrates relationships between pulling forces acting when artificial joint cups are detached from artificial bones and centroidal frequencies in a case in which installation rods are attached to the artificial joint cups attached to bones (artificial bones and human bones) and the installation rods are pulled; and relationships between pulling forces acting when artificial joint cups are detached from bones of donated bodies and centroidal frequencies in a case in which installation rods are attached to the artificial joint cups attached to the bones of donated bodies and the installation rods are pulled. According to FIG. 21, even when a bone of a donated body most similar to a living body is used, it can be seen that there is a correlation between the pulling force and the centroidal frequency, similar to the case in which an artificial bone is used. Therefore, a pulling force of the artificial joint cup can be estimated from the centroidal frequency.

Without being limited to artificial joint cups, regarding the implant 450 as well, estimation of a pulling force, an embedding torque, and a magnetic RFA measurement value (ISQ) may be performed using a centroidal frequency instead of a frequency peak.

In the second embodiment described above, a case in which the implant installation strength evaluation device 100b and the second laser system 250 are connected to each other through the cable 202 has been described, but it is not limited thereto. For example, the implant installation strength evaluation device 100b and the second laser system 250 may be connected to each other by radio.

In the second embodiment described above, a case in which the implant installation strength evaluation device 100b, the first laser system 200, and the second laser system 250 are separate devices has been described, but they are not limited to this example. For example, the first laser system 200 and the second laser system 250 may be included in the implant installation strength evaluation device 100b.

In the second embodiment described above, a case in which a pulling force is applied has been described as an example of the information indicating the index of the installation strength of the evaluation target 50, but it is not limited thereto. For example, information other than a pulling force may be used or information in which a pulling force and information other than a pulling force are combined may be used as the information indicating the index of the installation strength of the evaluation target 50.

In the second embodiment described above, a case in which a peak frequency at which the number of vibrations peaks is acquired from a frequency spectrum has been described, but it is not limited thereto. For example, a frequency corresponding to predetermined vibration may be acquired from a frequency spectrum.

In the second embodiment described above, a case in which the implant installation strength evaluation device 100b determines whether or not a pulling force is included within a range set in advance so that the pulling force is considered appropriate when it is included within the range and the pulling force is considered inappropriate when it is not included within the range has been described, but it is not limited to this example. For example, the pulling forces may be classified into three or more groups depending on values of the pulling forces and states of the classified pulling forces may be indicated.

According to at least the implant installation strength evaluation system of the second embodiment, the implant installation strength evaluation system vibrates an evaluation target when the evaluation target is irradiated with the laser beam A. Due to such a constitution, an evaluation target can be vibrated in a non-contact manner. For example, when a resonance frequency is acquired by vibrating an implant using a magnetic force in RFA, there is a need to install a jig having a magnet in the implant. Therefore, it is difficult to apply the method to orthopedic implants which are sometimes installed deep inside a body.

The implant installation strength evaluation system irradiates a vibrated evaluation target with the laser beam B1 and derives a frequency spectrum of vibration of the evaluation target based on the laser beam B2 that is the reflected laser beam B1 from the evaluation target. Due to such a constitution, a frequency spectrum of vibration of an evaluation target can be derived in a non-contact manner without attaching a device such as an acceleration sensor to the evaluation target.

The implant installation strength evaluation system acquires a peak frequency from a derived frequency spectrum and acquires a pulling force associated with the acquired peak frequency. Due to such a constitution, a pulling force reflecting a gap between an evaluation target and an installation rod attached to the evaluation target and a strength of the base can be acquired. Then, an evaluation result indicating whether or not the installation strength of the evaluation target 50 is appropriate can be acquired based on the pulling force.

The implant installation strength evaluation system is non-invasive so that it can be performed repeatedly, and deviation in a subject and between subjects can be reduced. In the implant installation strength evaluation system, since there is no need to install a jig having a magnet in an implant, the installation strength of the implant can be evaluated during a surgical operation. Until now, selection or an installation strength of an implant has had to rely on judgment of an operator, but the selection or the installation strength of an implant can be objective. Therefore, the success rate of a surgical operation can be improved without relying on the skill of an operator.

(Modification Example 1)

In the first embodiment and the second embodiment described above, a case in which a vibrated evaluation target is irradiated with the laser beam B1 and a frequency spectrum of vibration of the evaluation target 50 is derived based on the laser beam B2 that is the reflected laser beam B1 from the evaluation target 50 has been described. In an implant installation strength evaluation system of a modification example, vibration of the evaluation target 50 is detected by an acceleration sensor.

Figure 22:
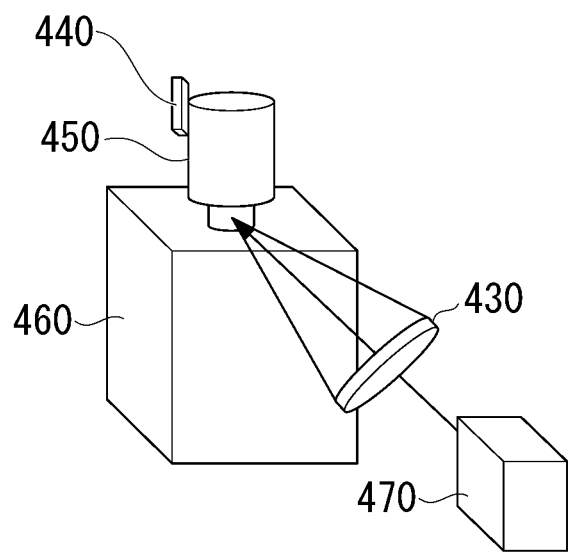
FIG. 22 is a view illustrating an implant installation strength evaluation system in an example (Example 5) according to a modification example.

FIG. 22 is a view illustrating an implant installation strength evaluation system in an example (Example 5) according to a modification example.

The implant installation strength evaluation system of the modification example includes the first laser system 470, a lens 430, the acceleration sensor 440, the implant 450, and the artificial bone 460.

The implant 450 is embedded in the artificial bone 460.

The first laser system 470 generates a laser beam for inducing vibration in the implant 450 and performs irradiation of the generated laser beam. The lens 430 condenses the irradiation laser beam of the first laser system 470. The root of the implant 450 is irradiated with the laser beam condensed by the lens 430. The implant 450 vibrates when the root of the implant 450 is irradiated with a laser beam. Specifically, an example of the first laser system 470 is a Nd:YAG laser, and laser energy may be set suitably within a range of 10 mJ to 30 mJ, for example. Typically, it may be within a range of 15 mJ to 25 mJ. In addition, a repetitive frequency of the laser is within a range of 5 Hz to 15 Hz. The average number of instances of spectra is within a range of 100 times to 150 times.

The acceleration sensor 440 is attached to the head portion of the implant 450 and detects the acceleration generated in the implant 450. The acceleration sensor 440 outputs information indicating the detected acceleration to a communication I/F of the implant installation strength evaluation device.

The implant installation strength evaluation device 100*a* can be applied as the implant installation strength evaluation device. However, the acquisition unit 132 acquires the information indicating the acceleration which is generated in the evaluation target 50 and is output by the communication I/F 105. The acquisition unit 132 outputs the acquired information indicating the acceleration which is generated in the evaluation target 50 to the deriving unit 134*a*. The deriving unit 134*a* derives the frequency spectrum of the number of vibrations and a vibration strength with respect to each of the vibration frequencies of the evaluation target 50 based on the information indicating the acceleration which is generated in the evaluation target 50 and is output by the acquisition unit 132.

According to operation of the implant installation strength evaluation device illustrated in FIG. 22, the implant installation strength evaluation device 100*a* acquires a peak frequency from the frequency spectrum of the number of vibrations and a vibration strength of the vibrated evaluation target 50. The implant installation strength evaluation device 100*a* acquires the embedding torque associated with the acquired peak frequency from association between peak frequencies and embedding torques. The implant installation strength evaluation device 100*a* acquires an evaluation result indicating whether or not the installation strength of the evaluation target 50 is appropriate from the acquired embedding torque. Due to such a constitution, similar to the first embodiment and the second embodiment described above, an evaluation result of the installation strength of an implant can be acquired in a non-contact manner.

(Modification Example 2)

In the first embodiment and the second embodiment described above, a case in which a vibrated evaluation target is irradiated with the laser beam B1 and a frequency spectrum of the number of vibrations and a vibration strength of the evaluation target 50 is derived based on the laser beam B1 that is the reflected laser beam B2 from the evaluation target 50 has been described. In an implant installation strength evaluation system of another modification example, a frequency spectrum of vibration of an evaluation target is derived by detecting a sound generated by the vibrated evaluation target 50. Air vibrates due to the vibrating evaluation target 50, and a sound is generated due to the vibrating air. The implant installation strength evaluation system detects this sound.

Figure 23:
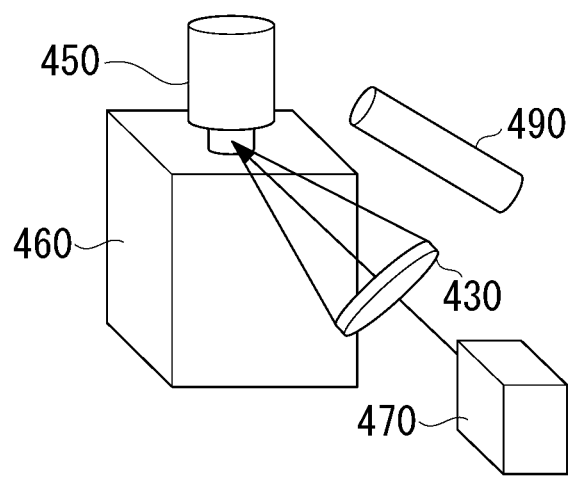
FIG. 23 is a view illustrating an implant installation strength evaluation system in an example (Example 6) according to another modification example.

FIG. 23 is a view illustrating an implant installation strength evaluation system in an example (Example 6) according to another modification example.

The implant installation strength evaluation system of the modification example includes the first laser system 470, the lens 430, the implant 450, the artificial bone 460, and a microphone 490.

The implant 450 is embedded in the artificial bone 460.

The first laser system 470 generates a laser beam for inducing vibration in the implant 450 and performs irradiation of the generated laser beam. The lens 430 condenses the irradiation laser beam of the first laser system 470. The root of the implant 450 is irradiated with the laser beam condensed by the lens 430. The implant 450 vibrates when the root of the implant 450 is irradiated with a laser beam. Specifically, an example of the first laser system 470 is a Nd:YAG laser, and laser energy may be set suitably within a range of 10 mJ to 30 mJ, for example. Typically, it may be within a range of 15 mJ to 25 mJ. In addition, a repetitive frequency of the laser is within a range of 5 Hz to 15 Hz. The average number of instances of spectra is within a range of 100 times to 150 times.

The microphone 490 detects a sound generated when the evaluation target 50 vibrates. The microphone 490 outputs information indicating the detected sound to the communication I/F of the implant installation strength evaluation device.

The implant installation strength evaluation device 100a can be applied as the implant installation strength evaluation device. However, the acquisition unit 132 acquires the information indicating the sound which is generated due to the vibrating evaluation target 50 and is output by the communication I/F 105. The acquisition unit 132 outputs the acquired information indicating the sound generated due to the vibrating evaluation target 50 to the deriving unit 134a. The deriving unit 134a derives a frequency spectrum of the number of vibrations and a vibration strength with respect to each of the vibration frequencies of the evaluation target 50 based on the information indicating the sound which is generated due to the vibrating evaluation target 50 and is output by the acquisition unit 132.

According to operation of the implant installation strength evaluation device illustrated in FIG. 23, the implant installation strength evaluation device 100a acquires a peak frequency from the frequency spectrum of vibration of the vibrated evaluation target 50. The implant installation strength evaluation device 100a acquires the embedding torque associated with the acquired peak frequency from association between peak frequencies and embedding torques. The implant installation strength evaluation device 100a acquires an evaluation result indicating whether or not the installation strength of the evaluation target 50 is appropriate from the acquired embedding torque. Due to such a constitution, similar to the first embodiment and the second embodiment described above, an evaluation result of the installation strength of an implant can be acquired in a non-contact manner.

In the first embodiment and the second embodiment described above, a case in which the evaluation target 50 is vibrated by irradiating the evaluation target with the laser beam A has been described, but it is not limited to this example. For example, the evaluation target 50 may be vibrated by applying a force to the evaluation target, such as applying a water stream using a waterjet or the like. In addition, for example, the evaluation target 50 may be vibrated by applying a force to the evaluation target, such as applying a physical impact using a hammer, a pendulum, or the like. In these cases, the vibrated evaluation target 50 may be irradiated with the laser beam B1. A frequency spectrum of vibration of the evaluation target 50 may be derived based on the laser beam B2 that is the reflected laser beam B1 from the evaluation target 50. A sound generated by vibrating air due to the vibrated evaluation target 50 may be detected using a microphone. A frequency spectrum of vibration of the evaluation target 50 may be derived using an acceleration sensor.

Hereinabove, the embodiments of the present invention have been described. However, these embodiments are provided as examples and are not intended to limit the scope of the invention. These embodiments can be performed in various other forms, and various omissions, replacements, changes, and combinations can be made within a range not departing from the gist of the invention. These embodiments and the modification examples thereof are included in the scope and the gist of the invention. At the same time, these embodiments and the modification examples thereof are included in the invention disclosed in the claims and within a range equivalent thereto.

The implant installation strength evaluation device 100a and the implant installation strength evaluation device 100b described above internally have a computer. Then, each process of the processing in each device described above is stored in a computer readable recording medium in a form of a program, and the processing is performed by the computer reading and executing this program. Here, a computer readable recording medium indicates a magnetic disk, an optical magnetic disc, a CD-ROM, a DVD-ROM, a semiconductor memory, or the like. In addition, this computer program may be distributed to a computer through a communication line, and the computer which has received this distribution may execute the program.

In addition, the program may realize a part of the functions described above. Moreover, the program may be able to be realized by combining the functions described above and the program which has already been recorded in a computer system, that is, a so-called differential file (differential program).

In the embodiments described above, the first laser systems are examples of vibration induction units, the second laser systems are examples of measurement units, the laser beam A is an example of a first laser beam, and the laser beam B is an example of a second laser beam.

REFERENCE SIGNS LIST 20, 450 Implant
21 Main body
22 Threaded portion
23 Head portion
23a Horizontal hole
23b Root
24 Bone
50 Evaluation target
100a, 100b Implant installation strength evaluation device
105 Communication I/F
110 Storage unit
112 Program
114a, 114b Derivative table
120 Operation unit
130a, 130b Information processing unit
132 Acquisition unit
134a, 134b Deriving unit
136a, 136b Evaluation unit
140 Display unit
150 Bus line
200, 470 First laser system
202 Cable
204, 206, 208 Optical fiber
250, 410 Second laser system
300 Irradiation head
420 First reflector
430 Lens
440 Acceleration sensor
460 Artificial bone
480 Second reflector
490 Microphone
495 Third reflector 500 Artificial joint cup
502 Outer surface
504 Inner surface
506 Hole
510 Probe

The invention claimed is:

1. An implant installation strength evaluation method comprising:
　a step of vibrating an implant when the implant is irradiated with a laser beam;
　a step of measuring time series data of the number of vibrations and vibration strengths of the implant vibrated in the vibrating step; and
　a step of deriving information indicating an index of an installation strength of the implant based on the time series data of the number of vibrations and the vibration strengths of the implant.

2. The implant installation strength evaluation method according to claim 1 further comprising:
　a step of acquiring an evaluation result of the installation strength of the implant based on the information indicating the index of the installation strength.

3. The implant installation strength evaluation method according to claim 1,
　wherein in the deriving step, a relationship between a frequency, the number of vibrations, and a vibration strength is obtained based on the time series data of the number of vibrations and the vibration strengths of the implant; a frequency corresponding to a predetermined number of vibrations and a predetermined vibration strength is obtained from the obtained relationship between a frequency, the number of vibrations, and a vibration strength; and the information indicating the index of the installation strength of the implant associated with the obtained frequency is obtained from association between the frequency and the information indicating the index of the installation strength of the implant.

4. The implant installation strength evaluation method according to claim 1,
　wherein at least one of the steps is controlled and executed by a computer.

5. The implant installation strength evaluation method according to claim 3,
　wherein the information indicating the index of the installation strength of the implant is an embedding torque indicating a resistance generated in a bone when the implant is embedded in the bone.

6. The implant installation strength evaluation method according to claim 3,
　wherein the information indicating the index of the installation strength of the implant is a pulling force that is a force acting when an artificial joint cup is detached from a bone in a case in which an installation rod is attached to the artificial joint cup attached to the bone and the installation rod is pulled.

7. The implant installation strength evaluation method according to claim 1,
　wherein in the measuring step, the time series data of the number of vibrations and vibration strengths of the implant vibrated in the vibrating step is measured using an acceleration sensor.

8. The implant installation strength evaluation method according to claim 1,
　wherein in the measuring step, the time series data of the number of vibrations and vibration strengths of the implant vibrated in the vibrating step is measured based on a generated sound.

9. The implant installation strength evaluation method according to claim 1,
　wherein in the vibrating step, the implant is vibrated when the implant is irradiated with a first laser beam, and
　wherein in the measuring step, the implant is irradiated with a second laser beam, and the time series data of the number of vibrations and vibration strengths of the implant is measured based on the second laser beam reflected by the implant.

10. The implant installation strength evaluation method according to claim 1,
　wherein in the vibrating step, the implant is vibrated by applying a water stream to the implant, and
　wherein in the measuring step, the time series data of vibration strengths of the implant is measured by applying a water stream to the implant based on a generated sound.

11. The implant installation strength evaluation method according to claim 1
　wherein the measuring step is executed by an implant installation strength evaluation device and is executed in a non-contact manner utilizing a laser beam.

12. An implant installation strength evaluation device acquiring data using the implant installation strength evaluation method according to claim 1, the device comprising:
　a vibration induction unit that vibrates an implant when the implant is irradiated with a laser beam;
　a measurement unit that measures time series data of the number of vibrations and vibration strengths of the implant vibrated by the vibration induction unit; and
　a deriving unit that derives information indicating an index of an installation strength of the implant based on the time series data of the number of vibrations and the vibration strengths of the implant measured by the measurement unit.

13. An implant installation strength evaluation device according to claim 12, wherein the measurement unit performs an action in a non-contact manner utilizing a laser beam.

14. A program for acquiring data using the implant installation strength evaluation device according to claim 12 by causing a computer to execute
　a step of vibrating an implant when the implant is irradiated with a laser beam,
　a step of measuring time series data of the number of vibrations and vibration strengths of the implant vibrated in the vibrating step, and
　a step of deriving information indicating an index of an installation strength of the implant based on the time series data of the number of vibrations and the vibration strengths of the implant,
　wherein both or any one of the vibrating step and the measuring step is executed in a non-contact manner utilizing a laser beam.

15. The implant installation strength evaluation method according to claim 1, wherein irradiation energy of the laser beam be set within a range of 1 mJ to 50 mJ.

16. The implant installation strength evaluation method according to claim 1, wherein the distance between the implant and the tip of the optical fiber that irradiates the laser beam is set within a range of 10 mm to 50 mm when a condensing optical element is mounted at the tip of the optical fiber.

17. The implant installation strength evaluation method according to claim 1, wherein the distance between the implant and the tip of the optical fiber that irradiates the laser beam is set within a range of 0.1 mm to 2 mm.

* * * * *